United States Patent
Aguilar et al.

(10) Patent No.: US 10,497,284 B2
(45) Date of Patent: Dec. 3, 2019

(54) SYSTEMS AND METHODS OF ULTRASOUND SIMULATION

(71) Applicant: THE GOVERNING COUNCIL OF THE UNIVERSITY OF TORONTO, Toronto (CA)

(72) Inventors: Luis Aguilar, Toronto (CA); DAvid Steinman, Toronto (CA); Richard Southwell Chevallier Cobbold, Toronto (CA)

(73) Assignee: THE GOVERNING COUNCIL OF THE UNIVERSITY OF TORONTO, Toronto (CA)

(*) Notice: Subject to any disclaimer, the term of this patent is extended or adjusted under 35 U.S.C. 154(b) by 78 days.

(21) Appl. No.: 15/559,693

(22) PCT Filed: Mar. 18, 2016

(86) PCT No.: PCT/CA2016/050304
§ 371 (c)(1),
(2) Date: Sep. 19, 2017

(87) PCT Pub. No.: WO2016/149805
PCT Pub. Date: Sep. 29, 2016

(65) Prior Publication Data
US 2018/0293913 A1 Oct. 11, 2018

Related U.S. Application Data

(60) Provisional application No. 62/135,925, filed on Mar. 20, 2015.

(51) Int. Cl.
*G09B 23/28* (2006.01)
*G01N 29/44* (2006.01)

(52) U.S. Cl.
CPC ....... *G09B 23/286* (2013.01); *G01N 29/4472* (2013.01)

(58) Field of Classification Search
CPC ...... G09B 23/286; G09B 23/28; G09B 23/30; A61B 2034/2063
See application file for complete search history.

(56) References Cited

U.S. PATENT DOCUMENTS 8,235,726 B2    8/2012    Hostettler et al.
8,480,404 B2    7/2013    Savitsky
(Continued)

FOREIGN PATENT DOCUMENTS

WO    2013082426 A1    6/2013

OTHER PUBLICATIONS

"Fast and mechanistic ultrasound simulation using a point source/receiver approach", IEEE Transactions on Ultrasonics, Ferroelectrics and Frequency Control, IEEE, US, vol. 60, No. 11, Nov. 1, 2013 (Nov. 1, 2013), pp. 2335-2346, XP011531206, ISSN:0885-3010, DOI: 10.1109/TUFFC.2013.6644737.
(Continued)

*Primary Examiner* — Omkar A Deodhar
(74) *Attorney, Agent, or Firm* — Anil Bhole; Marc Lampert; Bhole IP Law

(57) ABSTRACT

Herein described are systems and methods of ultrasound imaging. More particularly, embodiments described herein provide an ultrasound simulator based on the physics of ultrasound, such that it is possible to realistically reproduce most of the common characteristics of ultrasound examinations. Further, methods are described herein which may affect the computational efficiency of ultrasound simulation.

20 Claims, 18 Drawing Sheets

(56) References Cited

U.S. PATENT DOCUMENTS

| | | | |
|---|---|---|---|
| 2011/0306025 A1 | 12/2011 | Sheehan et al. | |
| 2012/0189998 A1 | 7/2012 | Kruecker et al. | |
| 2013/0323700 A1 | 12/2013 | Samosky et al. | |
| 2015/0056591 A1 | 2/2015 | Tepper et al. | |

OTHER PUBLICATIONS

Ramtin Shams et al: "An algorithm for efficient computation of spatial impulse response on the GPU with application in ultrasound simulation", 2011 8th IEEE International Symposium on Biomedical Imaging: From Nano to Macro (ISBI 2011), IEEE, United States, Mar. 30, 2011 (Mar. 30, 2011), pp. 45-51, XP031944484, DOI:10.1109/ISBI.2011.5872351 ISBN: 978-1-4244-4127-3.

Jorgen Arendt Jensen et al: "ambiguous encounters, uncertain foetuses: women's experiences of obstetric ultrasound", Imaging of Complex Media with Acoustic and Seismic Waves, Topics in Applied Physics, Jan. 1, 2016 (Jan. 1, 2016), XP055491097.

Jason F Kutarnia et al: "Virtual reality training system for diagnostic ultrasound", Ultrasonics Symposium (IUS), 2010 IEEE, IEEE, Oct. 11, 2010 (Oct. 11, 2010), pp. 1652-1656, XP031953082, DOI: 10.1109/ULTSYM.2010.5935947 ISBN: 978-1-4577-0382-9.

Extended European search report for application No. 16767572.7.

Aguilar Luis et al: "Famus Ii: a Fast and Mechanistic Ultrasound Simulator Using an Impulse Response Approach", IEEE Transactions on Ultrasonics, Ferroelectrics and Frequency Control, IEEE, US, vol. 64, No. 2, Feb. 1, 2017 (Feb. 1, 2017), pp. 362-373, XP011640319.

Sengupta, Shubhabrata, et al. (2007) Scan Primitives for GPU Computing, Proc. 22nd ACM SIGGRAPH/Eurographics Symposium on Graphics Hardware, pp. 97-106.

Ladner, R.E., at al. (1980) Parallel Prefix Computation, Journal of the ACM 27, 4:831-838.

Barber, C.B., et al. (1996) The Quickhull Algorithm for Convex Hulls, ACM Trans. Mathematical Software 22, 469-483.

Marius Muja, et al. (2014) Scalable Nearest Neighbor Algorithms for High Dimensional Data, Pattern Analysis and Machine Intelligence (PAMI), vol. 36.

Jensen, JA., et al. (1997) Acoustical Imaging, Springer, p. 75-80.

International Search Report corresponding to PCT/CA2016/050304; Canadian Intellectual Property Office; dated May 31, 2016.

Written Opinion of the International Searching Authority corresponding to PCT/CA2016/050304; Canadian Intellectual Property Office; dated May 31, 2016.

Blum T, Rieger A, Navab N, Friess H, Martignoni M. A Review of Computer-Based Simulators for Ultrasound Training. Simulation in Healthcare. 2013;8(2):98-108.

Ziv A, Wolpe PR, Small SD, Glick S. Simulation-based medical education: an ethical imperative. Academic Medicine. 2003;78(8):783-788.

Jensen JA. Speed-accuracy trade-offs in computing spatial impulse responses for simulating medical ultrasound imaging. Journal of Computational Acoustics. 2001;9(03):731-744.

Jensen JA. Field: A program for simulating ultrasound systems. Medical and Biological Engineering and Computing. 1996;Supplement 1, Part 1:351-353.

Jensen JA, Svendsen NB. Calculation of pressure fields from arbitrarily shaped, apodized, and excited ultrasound transducers. Ultrasonics, Ferroelectrics and Frequency Control, IEEE Transactions on. 1992;39(2):262-267.

Ahmad R, Kundu T, Placko D. Modeling of phased array transducers. The Journal of the Acoustical Society of America. 2005;117(4)1762-1776.

Aguilar LA, Steinman DA, Cobbold RS. On the Synthesis of Sample Volumes For Real-Time Spectral Doppler Ultrasound Simulation. Ultrasound in medicine & biology. 2010;36(12):2107-2116.

Aguilar LA, Cobbold RS, Steinman DA. Fast and Mechanistic Ultrasound Simulation Using a Point Source/Receiver Approach. IEEE Transactions in Ultrasonics, Ferroelectrics and Frequency Control. 2013;60(11):2335-2346.

Reichl T, Passenger J, Acosta O. Salvado O. Ultrasound goes GPU: real-time simulation using CUDA. In: SPIE Medical Imagin. International Society for Optics and Photonics; 2009. p. 726116:1-726116:10.

Gjerald SU, Brekken R, Hergum T, D'hooge J. Real-time ultrasound simulation using the GPU. Ultrasonics, Ferroelectrics and Frequency Control, IEEE Transactions on. 2012;59(5):885-892.

Piwakowski B, Delannoy B. Method for computing spatial pulse response: Time-domain approach. The Journal of the Acoustical Society of Amerca. 1989;86(6):2422-2432.

Piwakowski B, Sbai K. A new approach to calculate the field radiated from arbitrarily structured transducer arrays. Ultrasonics, Ferroelectrics and Frequency Control, IEEE Transactions on. 1999;46(2):422-440.

Jensen JA, Gandhi D, O'Brien Jr WD. Ultrasound fields in an attenuating medium. In: Ultrasonics Symposium, 1993. Proceedings., IEEE 1993. IEEE; 1993. p. 943-946.

Gurumurthy KV, Arthur RM. A Dispersive Model for the Propagation of Ultrasound in Soft Tissue. Ultrasonic Imaging. 1982;(4):355-377.

Jensen JA. Users guide for the Field II Program. Technical University of Lyngby/Denmark. 2011.

Jensen JA, Munk P. Computer phantoms for simulating ultrasound B-mode and cfm images. In: Acoustical Imaging. Springer; 1997. p. 75-80.

600

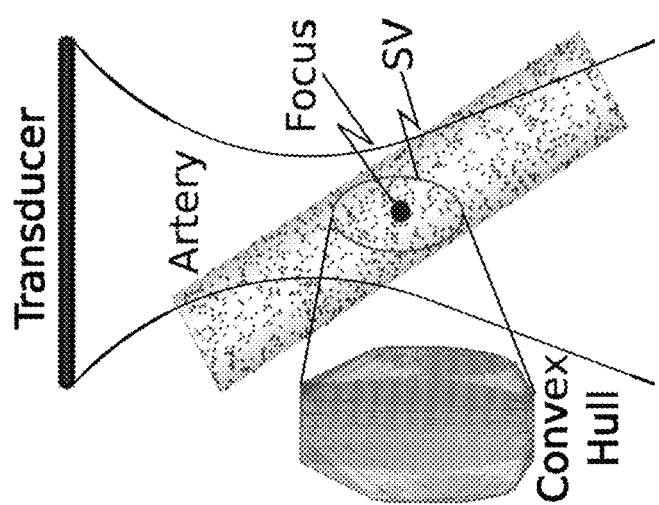
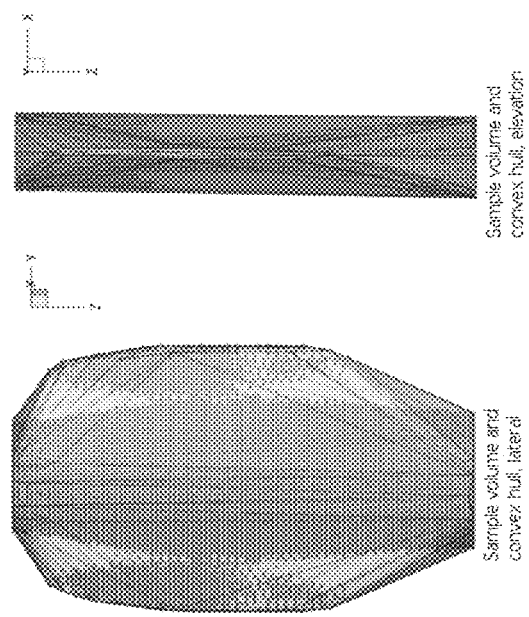
FIG. 9B
FIG. 9A

SYSTEMS AND METHODS OF ULTRASOUND SIMULATION

TECHNICAL FIELD

The following described embodiments relate generally to systems and methods of ultrasound simulation.

BACKGROUND

Ultrasound imaging modalities are based on the scattering of acoustic energy by interfaces of tissue materials having different properties through interactions governed by acoustic physics. These interactions provide the information needed to generate high-resolution, gray-scale images of the body (e.g., B-mode images) as well as to display information on blood flow (e.g., Color-Doppler and Power Mode images). When an acoustic wave is emitted into a material, the amplitude of the reflected energy is used to generate ultrasound images, and frequency shifts in the backscattered ultrasound signals that provide provides information relating to moving targets such as blood.

Ultrasound imaging is a medical imaging modality whose accuracy can be highly operator-dependent. Ultrasound system operators include sonographers, doctors, medical students, radiology specialists and medical technologists. Successful examination with an ultrasound imaging system by an ultrasound system operator involves specific skills on the part of the operator, including good hand-eye coordination, correct localization of a region of interest (e.g., a target organ), accurate interpretation of ultrasound images, correct use of ultrasound system modes, basic knowledge of the physics of ultrasound complemented with a good understanding of the image generation process, and excellent knowledge of the setup of the ultrasound system parameters and imaging conditions. The number of different parameters that can be set up in any ultrasound system makes image acquisition and interpretation a challenging task. Moreover, the characteristic speckle pattern of all ultrasound images and the various artifacts commonly encountered in clinical practice makes this process even more difficult.

Ultrasound imaging simulators are becoming increasingly important in the training of ultrasound system operators. However, most existing simulators do not consider the physics of ultrasound acquisition and exhibit unrealistic processing time such that they do not closely simulate actual application of ultrasound in a clinical setting.

SUMMARY

In one aspect, a method for simulating ultrasound imaging is provided, the method comprising storing a model of a sham ultrasound transducer held by an operator during a simulated ultrasound procedure as a plurality of point sources for emitting a simulated acoustic wave during the simulated ultrasound procedure, storing an ultrasound target model, calculating a plurality of radio-frequency signals by repeatedly calculating the emission of a simulated acoustic wave signal from each point source to a subset of the ultrasound target model, calculating a transmitted impulse response for the subset of the ultrasound target model, calculating an overall transmitted impulse by aggregating the transmitted impulse responses, calculating an overall transmit-receive impulse response from the overall transmitted impulse response, and calculating a radio frequency signal from the overall transmit-receive impulse response, and generating an ultrasound image for output to a display from the plurality of radio frequency signals.

The ultrasound target model can comprise a plurality of point scatterers, the emission can be calculated from each point source to each point scatterer in the subset of the ultrasound target model, and the transmitted pulse response can be calculated for each point scatterer in the subset of the ultrasound target model.

The calculating the transmitted impulse response for each point scatterer can comprise using a phase of each acoustic wave signal between each point source and each point scatterer in the subset to compute a plurality of impulses, the phase being proportional to a distance between each point source in the subset and each point reflector.

The method can further comprise receiving pre-computed computational fluid dynamics flow information for the ultrasound target, associating the pre-computed computational fluid dynamics information with each point scatterer of the subset, and outputting a Doppler ultrasound image by post processing the plurality of radiofrequency signals and the computational fluid dynamics information.

The ultrasound target can comprise a three-dimensional model of an organ and the plurality of point scatterers are randomly distributed within the three-dimensional model of the organ.

The method can further comprise segmenting the ultrasound target model into a plurality of regions, associating each point scatterer with one of the plurality of regions, defining a sample volume as a volume where simulated acoustic energy from the simulated acoustic wave is concentrated during a simulated ultrasound procedure, determining a subset of the plurality of regions that fully encompass the sample volume, and determining the subset of the point scatterers associated with the subset of the plurality of regions during a simulated ultrasound procedure.

The method can further comprise defining a sample volume as a volume where simulated acoustic energy from the simulated acoustic wave exceeds a predetermined threshold criterion, the threshold criterion being proportional to the power of the simulated acoustic energy, and determining the subset of the point scatterers that fall within the sample volume.

The ultrasound target model can comprise a three-dimensional ("3D") triangulated surface mesh, the emission of the simulated acoustic wave can be calculated via ray-tracing from each point source to the 3D triangulated surface mesh, and the transmitted impulse can be calculated for each ray from the 3D triangulated surface mesh.

The calculating a plurality of radio-frequency signals can comprise determining the position and orientation of the sham transducer relative to the simulated location of an ultrasound target via a 3D position sensor and a 3D positioning reference module.

The calculating an overall transmit-receive impulse response can comprise self-convoluting the overall transmitted impulse response.

A first of the plurality of radio frequency signals can be carried out on a first processor and a second of the plurality of radio frequency signals can be carried out on a second processor.

The method can further comprise reproducing the behaviour or appearance of particular ultrasound systems via plug-in software modules.

Each point scatterer in the subset can be associated with a reflection coefficient for a given tissue within which each point scatterer in the subset is located.

The method can further comprise aligning the radio frequency signals, and computing an envelope of the radio frequency signals. The aligning can comprise filling the radio frequency signals with null information. The method can further comprise applying a lowpass interpolating filter among the radio frequency signals to expand the sequence.

In another aspect, a system for simulating ultrasound imaging is provided, the system comprising at least one processor, storage storing a model of a sham ultrasound transducer held by an operator during a simulated ultrasound procedure as a plurality of point sources for emitting a simulated acoustic wave during the simulated ultrasound procedure, and an ultrasound target model, and computer-readable instructions that, when executed by the at least one processor, cause the processor to calculate a plurality of radio-frequency signals by repeatedly calculate the emission of a simulated acoustic wave signal from each point source to a subset of the ultrasound target model, calculate a transmitted impulse response for the subset of the ultrasound target model, calculate an overall transmitted impulse by aggregating the transmitted impulse responses, calculate an overall transmit-receive impulse response from the overall transmitted impulse response, and calculate a radio frequency signal from the overall transmit-receive impulse response, and generate an ultrasound image for output to a display from the plurality of radio frequency signals.

The ultrasound target model can comprise a plurality of point scatterers, the emission of the simulated acoustic can be calculated from each point source to each point scatterer in the subset of the ultrasound target model, and the transmitted impulse response can be calculated for each point scatterer in the subset of the ultrasound target model.

The computer-readable instructions, when executed, can cause the at least one processor to use a phase of each acoustic wave signal between each point source and each point scatterer in the subset to compute a plurality of impulses, the phase being proportional to a distance between each point source in the subset and each point reflector.

The computer-readable instructions, when executed, can cause the at least one processor to receive pre-computed computational fluid dynamics flow information for the ultrasound target, associate the pre-computed computational fluid dynamics information with each point scatterer of the subset, and output a Doppler ultrasound image by post processing the plurality of radiofrequency signals and the computational fluid dynamics information.

The ultrasound target can comprise a 3D model of an organ and the plurality of point scatterers can be randomly distributed within the 3D model of the organ.

The computer-readable instructions, when executed, can cause the at least one processor to segment the ultrasound target model into a plurality of regions, associate each point scatterer with one of the plurality of regions, define a sample volume as a volume where simulated acoustic energy from the simulated acoustic wave is concentrated during a simulated ultrasound procedure, determine a subset of the plurality of regions that fully encompass the sample volume, and determine the subset of the point scatterers associated with the subset of the plurality of regions during a simulated ultrasound procedure.

The computer-readable instructions, when executed, can cause the at least one processor to define a sample volume as a volume where simulated acoustic energy from the simulated acoustic wave exceeds a predetermined threshold criterion, the threshold criterion being proportional to the power of the simulated acoustic energy, and determine the subset of the point scatterers that fall within the sample volume.

The ultrasound target model can comprise a 3D triangulated surface mesh, and the computer-readable instructions, when executed, can cause the at least one processor to calculate the emission of the simulated acoustic via ray-tracing from each point source to the 3D triangulated surface mesh, and calculate the transmitted impulse response for each ray from the 3D triangulated surface mesh.

The computer-readable instructions, when executed, can cause the at least one processor to determine the position and orientation of the sham transducer relative to the simulated location of an ultrasound target via a 3D position sensor and a 3D positioning reference module.

The computer-readable instructions, when executed, can cause the at least one processor to calculate the overall transmit-receive impulse response by self-convoluting the overall transmitted impulse response.

A first of the plurality of radio frequency signals can be carried out on a first processor and a second of the plurality of radio frequency signals can be carried out on a second processor.

The system can further comprise a sham transducer.

The system can further comprise plug-in software modules to enable the system to reproduce the behaviour or appearance of particular ultrasound systems.

Each point scatterer in the subset can be associated with a reflection coefficient for a given tissue within which each point scatterer in the subset is located.

The computer-readable instructions, when executed, can cause the at least one processor to align the radio frequency signals, and compute an envelope of the radio frequency signals. The aligning can comprise filling the radio frequency signals with null information. A lowpass interpolating filter can be applied among the radio frequency signals to expand the sequence.

In a further aspect, a method for simulating ultrasound imaging is provided, the method comprising storing a model of a sham ultrasound transducer held by an operator during a simulated ultrasound procedure as a plurality of point sources for emitting a simulated acoustic wave and as a fixed volume of transducer scatterers, the transducer scatterers being in a fixed spatial relationship from the plurality of point sources, storing a model of an ultrasound target as a plurality of model scatterers, wherein each model scatterer has an associated reflection coefficient, pre-computing impulse responses for each transducer scatterer in the fixed volume of transducer scatterers to a simulated acoustic wave emitted from the plurality of point sources, and upon the fixed volume of transducer scatterers at least partly intersecting the plurality of model scatterers during the simulated ultrasound procedure determining, for each transducer scatterer, a nearest neighbor model scatterer, assuming, for each transducer scatterer, the associated reflection coefficient of its nearest neighbor scatterer, and scaling the pre-computed impulse responses with the associated reflection coefficients.

These and other aspects are contemplated and described herein. It will be appreciated that the foregoing summary sets out representative aspects of systems and methods for simulating ultrasound imaging to assist skilled readers in understanding the following detailed description.

DESCRIPTION OF THE DRAWINGS

A greater understanding of the embodiments will be had with reference to the Figures, in which:

FIG. 9A illustrates a convex hull location in a segmented ultrasound target model; and FIG. 9B illustrates a convex hull;

DETAILED DESCRIPTION

Figure 1:
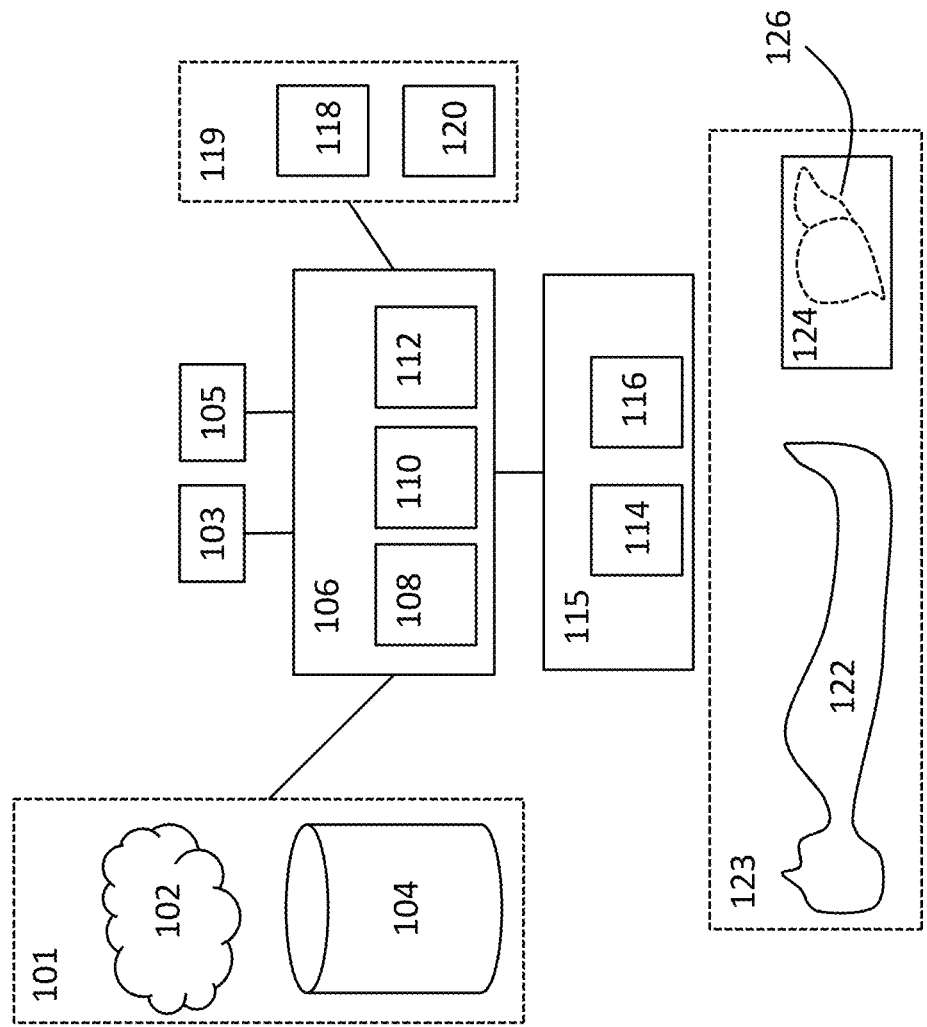
FIG. 1 illustrates components of a system for simulating ultrasound imaging in accordance with an embodiment.

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practised without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender. Further definitions for terms may be set out herein; these may apply to prior and subsequent instances of those terms, as will be understood from a reading of the present description.

Any module, unit, component, server, computer, terminal or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer-readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors. Further, any computer storage media and/or processors may be provided on a single application-specific integrated circuit, separate integrated circuits, or other circuits configured for executing instructions and providing functionality as described below.

A vital attribute of any ultrasound simulator used for training is the ability to present a physical situation in a realistic manner. Realistic presentation requires that a simulation react quickly, ideally on a substantially real-time basis. Ideally, any changes to transducer position and associated field response should be simulated with a sufficient degree of accuracy and speed. However, modeling the physics of ultrasound is computationally intensive.

The following provides systems and methods of ultrasound simulation. More particularly, embodiments described herein provide an ultrasound simulator based on the physics of ultrasound, such that it is possible to realistically reproduce most of the common characteristics of clinical ultrasound examinations. Furthermore, various ultrasound modes (e.g. Doppler mode, power mode) can be simulated using components of the system and methods described herein. Though embodiments below have been described with regard, in some cases, to particular ultrasound modes, it will be appreciated that the described systems and methods are applicable to simulation of other ultrasound modes. The systems implement a transducer model as an array of point sources in the imaging simulation and an ultrasound target model as a plurality of point scatters (also referred to herein as point reflectors) allowing realistic simulation of ultrasound physics that provide all ultrasound modes and artifacts. In aspects, the point scatterers are modelled volumetrically. In further aspects, the point scatterers are modelled along a tissue/organ interface surface for an organ of interest.

In the following, the components and functionality of a system for simulating ultrasound imaging are described. Further, methods are described which may improve the efficiency of ultrasound simulation, which may help to provide substantially real-time simulation.

Referring now to FIG. 1, a system 100 for ultrasound simulation in accordance with an embodiment is shown, the components and functionality of which will be described in more detail below. The illustrated embodiment of the system 100 comprises a database 101, an ultrasound simulator module 106, a probe module 115 comprising a sham transducer 114, an ultrasound target 123, a user interface module 119, and one or more processors 105, hereinafter referred to as processor 105. The processor 105 can be one or more central processing units ("CPUs"), one or more graphics processing units ("GPUs"), or a combination of both. The components of the system 100 are communicatively linked to the processor 105.

The ultrasound simulator module 106 receives input parameters and operator commands input by the operator at a control panel 118 of the user interface module 119, computational three-dimensional ("3D") models of the human body or relevant portions thereof (e.g., organs) from the storage device 101 relating to the ultrasound target 123, and 3D positioning and orientation information for the sham transducer 114. The ultrasound simulator module 106 processes the inputs to generate an ultrasound image as an output to a display 120.

In use, an operator (not shown) manipulates the sham transducer 114 about an ultrasound target 123. The ultrasound simulator module 106 simulates an ultrasound image according to methods as described in more detail below, which rely on simulation of the physics of ultrasound wave propagation. More specifically, for a given position of the sham transducer 114 about a target 123 associated with a 3D model of at least a part of the human body, an ultrasound wave is simulated to be transmitted from a model of the sham transducer 114 into the 3D model, and a received signal is calculated (referred to as RF signal, which is simulated), the received signal being a simulated reflection of the ultrasound wave off of a plurality of scatters distributed within the 3D model as described below. The RF signal may be post-processed by the ultrasound simulator module 106 to provide an ultrasound image for display on the display 120 of the user interface module 119.

In the following, the components and functionality of the system 100 are described, and then particular methods of simulating ultrasound waves, and reducing the computational burden of such a simulation, are set out in additional detail.

In embodiments, the database 101 stores computational 3D models of the human body, or portions thereof, for use as inputs to the ultrasound simulator module 106. The 3D models can relate to normal and abnormal human anatomies. In embodiments, each 3D model relating to an abnormal human anatomy may be associated with a particular clinical case. The database 101 comprises a cloud-based database 102 and/or a local database 104. Information in the database 101 can thus be stored locally on a storage device of the local database 104 or accessed via internet cloud-based storage infrastructure on the cloud-accessible database 102.

In embodiments, the probe module 115 comprises a sham transducer 114. The sham transducer may mimic the look and feel of a real ultrasound transducer. In use, the operator moves the sham transducer 114 over the ultrasound target 123. The probe module may also comprise a sham needle 116. In a real ultrasound system, the operator manipulates a transducer probe over a patient until it is positioned at a correct position for a region that the operator desires to study. The operator may determine that the transducer probe is correctly positioned by monitoring ultrasound images provided on a display. Similarly, in an ultrasound-guided needle insertion procedure, the operator inserts a needle in a desired part of the body of a patient and reviews generated ultrasound images to verify the position of the needle.

The system 100 mirrors the functionality of a real ultrasound procedure. In embodiments, a 3D position sensor is included in the ultrasound target 123 and/or the sham transducer 114 and/or sham needle 116 to determine the position and orientation of the sham transducer 114 and/or sham needle 116 relative to the ultrasound target 123. Each 3D position sensor may cooperate with a 3D positioning reference module 103, of known or determinable location, communicatively linked to the ultrasound simulator module 106. Each 3D positioning sensor is configured to communicate with the 3D positioning reference module 103 to provide its position relative to the 3D positioning reference module 103.

In embodiments, the 3D position sensors may provide sensor readings that can be processed to determine the spatial position and orientation of each component relative to the others on a reference coordinate system. The determined spatial position and orientation of components of the probe module 115 and the target 123 may be provided to the ultrasound simulator module 106 as inputs. In embodiments, before use, the system may be calibrated using a 3D position sensor of at least one of the above-described components, providing a global spatial coordinate system within which the target 123, the transducer 114 and the sham needle can be located. An exemplary calibration technique could be to (a) provide or determine the location of the 3D position sensor relative to the 3D positioning reference module 103, which can be accomplished using a variety of existing techniques, and to correspondingly establish a reference coordinate system; and (b) provide or determine the position of the target 123 in reference to the coordinate system. The latter may, for example, be provided by instructing a clinician, via the user interface module 119, to position the sham transducer along the surface of the target 123 at a plurality of predefined locations. Preferably, three or more such locations are obtained.

A 3D computational model of an organ may thus be simulated with respect to the position of the target 123 and components of the probe module 115. During a simulation, the operator can coordinate her hand movement and associated positioning of the sham transducer and optionally the sham needle by referring to ultrasound images displayed to the display 120, illustrating the relative position of a 3D computational model of an organ associated with a target 123, the sham transducer 114, and of the needle 116. Where included, the sham needle will appear on the simulated ultrasound image, such as a B-mode image, so that an operator will be able to make the necessary corrections. It will thus be understood that when generating ultrasound images, the ultrasound simulator module 106 will retrieve from the database appropriate 3D computational models of the human body for a given ultrasound target 123 in order to correctly illustrate the relative position of the sham transducer and needle therefrom. More particularly, an anatomy selection filter will select the region for which ultrasound simulation and associated computations described below will be carried out, by correlating the position and orientation information from the probe module 115, and information from the 3D models, received from the database 101.

The ultrasound target 123 comprises a physical reference with which the operator can practice. More specifically, the ultrasound target 123 comprises a physical reference around which the operator can move the sham transducer 114 in order to model and generate ultrasound images relating to a target, such as an organ of interest, within the ultrasound target 123. In embodiments, the ultrasound target 123 comprises a mannequin 122 or a virtual phantom box 124. The mannequin 122 may be a full body or partial body human mannequin that helps the operator to learn and practice the positioning of the transducer 114 with respect to approximately human anatomy. The virtual phantom box 124 may be similar to existing and commonly used ultrasound training phantoms. However, unlike traditional phantoms that may be designed exclusively for ultrasound simulation of a specific organ, the virtual phantom box 124 provides a virtual phantom 126 for any organ, provided an appropriate computational 3D model retrieved from the database 101 by the ultrasound simulator 106. The versatility of the virtual phantom box 124 has evident implications for cost savings.

The user interface device 119 comprises a control panel 118 and a display 120. The control panel 118 allows input of input parameters to the system by an operator. The control panel 118 may comprise any appropriate user input device, such as a touchscreen monitor. The control panel has input parameters that affect the ultrasound simulation (e.g. ultrasound mode, transducer frequency, gain selector, pulse repetition frequency (PRF), focal zone, color scale, wall filter value, size of the region of interest, etc.). The display 120 displays ultrasound images generated by the ultrasound simulator module 106 and may provide a graphical user interface (GUI) similar to that of a real ultrasound machine. In embodiments, plug-in software modules are stored in the database 101. Plug-in software modules may enable the system 100, and more particularly the control panel 118 and display 120, to reproduce the behavior and appearance of particular commercial ultrasound system to enhance the simulation experience. These plug-ins may vary the user inputs provided on the control panel 118 to correspond to user inputs of a variety of ultrasound equipment manufacturer, such as Toshiba™, Siemens™ GE™, Hitachi™, etc. Further, the plug-ins may vary the information and layout of the GUI of the display 120.

In embodiments, the illustrated ultrasound simulator module 106 comprises a wave simulator module 108, an RF (radio-frequency) post processing module 110 and a flow simulator module 112.

Methods of generating an RF signal by the wave simulator module 108, for use in generating an ultrasound image, will now be described. The generated RF signals are processed by a post processing module 110 to generate simulated images for ultrasound modalities, including but not limited to B-Mode, color-Doppler mode and power mode. As described above, the inputs to the simulator 106 include the parameters and operator commands from the control panel 118, the computational 3D models of the human body from the database 101, whether normal (i.e. healthy) or abnormal (i.e. modified with some pathological case), and the 3D positioning and orientation information from the probe module 115. The output is the generated ultrasound image.

According to a first method of generating an RF signal, the geometry of a transducer is modeled in a 3D space and point-sources are virtually placed at an emission surface of the transducer. From every point-source, a simulated acoustic wave, which mimics the shape and amplitude of the excitation pulse in a real ultrasound system, is emanated towards a volume of point-reflectors (scatterers) in an ultrasound target, each point-reflector being associated with ultrasound characteristics of tissue at the position of the point-reflector in a 3D model of the ultrasound target. The transmitted signals from all point-sources to a specific point-reflector are computed according to the particular point-source to point-reflector phase, which is proportional to its Euclidean distance. This process is done for all point-reflectors that compose a given tissue. In a second step, all point-reflectors act as point-sources and the previous point-sources act as point-reflectors. The RF signal is then calculated, such as by a summation of all received signals according to their specific phases (which are proportional to the distance of the point scatterer to the closest point source). It will be understood that this method may be repeated to generate additional RF signals. This method may provide for faster computing than traditional ultrasound simulation techniques, such as Field II software.

For estimating the transmit/receive (T/R) response of an ultrasound transducer array and an associated volume of scatterers, a software program called Field II is generally considered to yield images that are quite similar to those seen in clinical practice. Field II software is based on calculating transducer impulse response. Because of the need to model impulse response calculations for a dense scatterer distribution to achieve realistic results, i.e. typically more than 10 scatterers per $mm^3$ of a modeled tissue phantom, and the difficulty of parallelizing the algorithm, computation times can be in the order of hours to generate a simulated ultrasound image, whereas times in the order of a fraction of a second are desired.

Figure 2A:
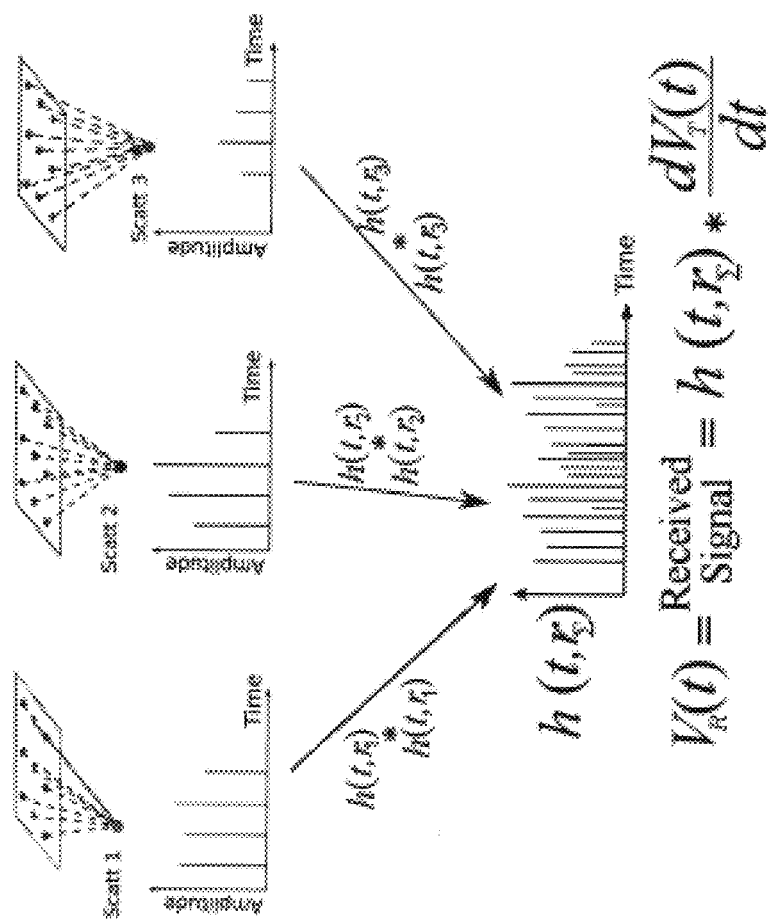
FIG. 2A illustrates a simplified method of generating a radio-frequency signal for use in simulating an ultrasound image.
Figure 2B:
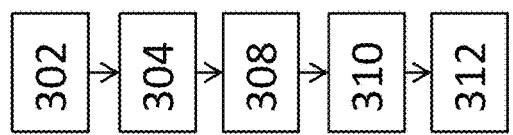
FIG. 2B is a flowchart of a simplified method of generating a radio-frequency signal for use in simulating an ultrasound image.

Referring now to FIGS. 2A to 2B, shown therein are illustrations of a method 300 for implementation in wave simulator 108 to generate RF signals, which will now be described in brief, and which will be described in additional detail below. This method may achieve fast computation times relative to other known ultrasound simulation techniques relying on the physics of ultrasound. Further, the method 300 may give close agreement with ultrasound images generated by Field II for both B-mode and spectral Doppler flow simulations, with reduced computational time for comparable ultrasound image quality.

FIG. 2A illustrates a simplified representation of a method 300 in which virtualized point scatterers in a 3D model of the ultrasound target are insonated by an array of virtualized point sources. FIG. 2B illustrates the method 300 as a flowchart. In brief, the method assumes that if each source radiates an impulse, a Dirac delta function arriving at each scatterer will have an arrival time that depends on the distance and speed of sound, and an amplitude that depends on the path length and attenuation. The sequence of all such impulses, when self-convoluted, is proportional to the transmit/receive (T/R) impulse response. As the number of point sources/receivers is increased, it can be expected that the T/R response will approach the true response. Rather than summing the emanated excitations pulses as described in relation to the first method above, the impulse response is computed by using the individual phases, which are proportional to the distances, for every point source-point reflector combination.

More particularly, according to method 300, at block 302, the sham transducer 114 is modeled as a collection of point sources and the 3D model of a tissue of an ultrasound target 123 is modeled with a volume of point reflectors (also referred to as scatterers), each reflector being associated with ultrasound characteristics of tissue at the position of the reflector in the 3D model (e.g. reflection coefficient). At block 304, a simulated acoustic wave is emitted from every point source towards the point reflectors. More particularly, a subset of transducer elements may be activated at a given time, irradiating a partial region (known as a line), as shown in FIG. 7A, and described in more detail below. At block 306, an impulse response is computed for each reflector by using the individual phases of each signal, wherein each phase is proportional to a distance for every point source to point reflector combination. A simplified illustration of this computation is illustrated in FIG. 2A. The phase of each signal is used to locate an impulse (vertical line) on the time axis. The amplitude of each impulse is proportional to the reciprocal distance of a given point source-point reflector combination. The ensemble of impulses for all point sources to a given point reflector is known as the transmit impulse response. The top leftmost graph in FIG. 2A corresponds to the impulse response of a particular point reflector illustrated as Scatt 1 (i.e. Scatterer 1). Impulse responses for remaining point reflectors are also calculated, illustrated for Scatt 2 and Scatt 3. At block 308, the impulse responses may be summed so that a total impulse response for all point reflectors from all point sources is computed as $h(t, r_\Sigma)$, referred to as the overall transmit impulse response. At block 310, a convolution operation is computed $h(t, r_1)*h(t, r_1)$ to provide a corresponding transmit-receive impulse response for a single scatterer, where the overall transmit-receive impulse response is computed as $h_\Sigma(t, r)*h_\Sigma(t, r)$. At block 312, another convolution operation is then performed on the overall transmit-receive impulse response and the emitted excitation signal. This convolution is illustrated at the bottom of FIG. 2 and is indicated by $V_R(t)$. The term $V_R(t)$ is referred to as the received voltage signal (or RF signal) for all point reflectors and all point sources. It will be understood that this method may be repeated to generate additional RF signals.

Due to the fact that the ultrasound simulator is based on the physics of ultrasound, it can generate a simulated RF signal similar to that of a real ultrasound system. This realism is achieved because various parameters that affect the behavior of the transducer may be modeled and varied, such as the particular transducer geometry, frequency of the transducer, lateral and elevation focal location, time gate filter, and time-gain compensation.

Once the RF signal is determined by the simulator module 108, it may be processed so that an image or a characteristic curve can be computed to present it to the operator at the display 120. Post-processing can be performed by the post-processing module 110, such as by applying post-processing algorithms, in a similar manner to real ultrasound systems. Different parameters for the post-processing and post-processing algorithms can be used and the effects will be observed in the ultrasound images displayed on the display 120.

Figure 3:
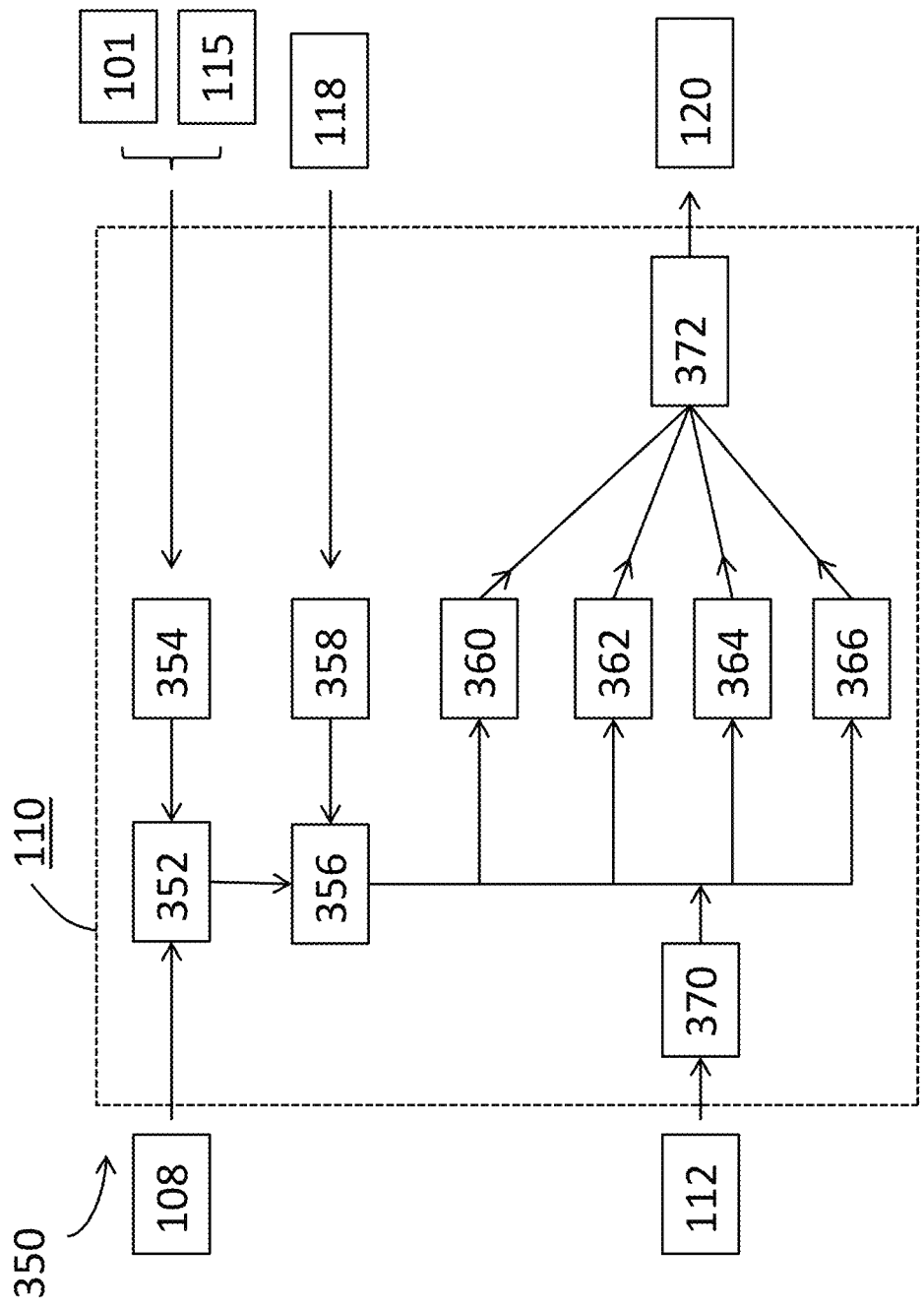
FIG. 3 is a flowchart illustrating a method of post-processing a radio-frequency signal.

Referring now to FIG. 3, shown therein is a flowchart illustrating a method 350 of post-processing by RF post processing module 110.

The module 110 receives a series of inputs in order to carry out post processing on the RF signal and to generate ultrasound images for output to display 120. At block 352, the RF signal generated by the acoustic wave simulator module 108 is provided as an input. At block 354, an anatomy filter receives 3D model information from the database 101 and position and orientation information from the probe module 115 to determine the part of the 3D model that was used to compute the RF signals. At block 352, the anatomy filter provides the 3D model information and position and orientation information to the post-processing module 110. At block 358, the module 110 also receives input parameters provided by the operator through the control panel 118 which may relate to simulation parameters.

At block 356, a beamformer receives the RF signal, 3D model information and position and orientation information of the probe module 115 and the input parameters provided by the operator. Further at block 356, the beamformer processes received information and aligns the generated RF signals in a form that will correspond to the specific ultrasound mode. The alignment is described in more detail below with regard to block 360. The output from the beamformer is used as input information to the different ultrasound modes.

At blocks 360, 362, 364, and 366 the outputs from the beamformer are processed to provide a specific ultrasound mode, such as B-mode (block 360), color Doppler (block 362), spectral Doppler (block 364) or power Doppler (block 366). At block 372, a mode selector determines which ultrasound mode will be provided as a system output and displayed to a display 120.

By way of example, in the case of B-mode (block 360), a number of RF signals are received from the wave simulator module 108 and processed to generate a B-mode image. A minimum of 50 signals may be required to generate a B-mode image. Specifically, the RF signals are received by the post-processing module, aligned by the beamformer (block 356) and an envelope of the RF signals is computed. Signal processing techniques, such as Discrete Fourier Transforms (DFT) and Hilbert transforms are used to determine the envelope of the signals. Because the RF signals do not have the same length and also have different starting times, the RF post processing module must align them, such as by filling them with null information, i.e. zeros, at the beginning and at the end. This alignment may be done accordingly to the minimum distance (or equivalently, the minimum arriving time) from the transducer to the closest scatterer (from a collection of many) used to compute that line. Then, for all lines, zeros may be added at the beginning and at the end in such a way that all signals start and end at the same instant in time. In this way, all RF signals will have the same length and the same starting time. Then, a lowpass interpolating filter may be applied among the RF lines to expand the sequence. The net effect may be an increase in resolution of the B-mode image. A B-mode image may then be created and displayed to the display 120.

Further by way of example, to generate color Doppler (block 362) or spectral Doppler (block 364) modes, the post-processing module must receive information relating to simulated blood flow, as explained in more detail below. At block 370, the module 110 first receives velocity information from a blood flow simulation provided by flow simulation module 112 at block 370 and RF signals from the ultrasound simulation module 108 at block 352. The number of RF signals received will depend on the pulse repetition frequency selected by the operator at the control panel 118, i.e. the temporal resolution of the simulation. In the case of color Doppler (block 362), an image is generated using a color scale that is proportional to the blood flow velocity at locations in the ultrasound target, and corresponding to the 3D model. The color Doppler information can be displayed overlapping on a B-mode image on a GUI of the display 120. For generating a spectral Doppler image (364), received RF signals are used to build a spectrogram curve representing the velocity in time for a given location in the ultrasound target. The spectrogram may be displayed overlapping a B-mode image on a GUI of the display 120.

CFD (Computational Fluid Dynamics) is a set of techniques that realistically simulate the flow behavior of a fluid in a complex geometry, which is the case of the simulation of blood flow in arteries. CFD divides the target geometry into small, regular-shaped elements where the equations of fluid flow are solved for a number of time steps. However, CFD requires the use of small time steps and an unstructured mesh of a great number of elements to accurately approximate the blood flow response in a complex arterial geometry, as is the case in image-based arterial 3D models. Owing to the high computational burden of performing CFD, simulating this type of flow in real-time is problematic.

Figure 4:
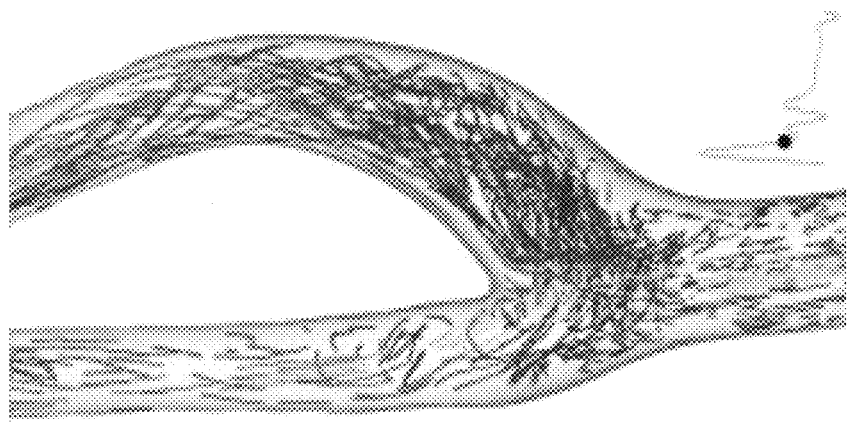
FIG. 4 illustrates a computational fluid dynamics representation of a realistic arterial geometry and its associated velocity field.

Block (370) in FIG. 3 illustrates that output from a blood flow simulation module 112 may be used as an input to the post processing module 110 at least at blocks (362) and (364) to generate color Doppler and spectral Doppler images. Because the system 100 provides simulations based on the physics of ultrasound, simulations from system 100 can be combined with other physics-based simulations, such as simulations provided by CFD. CFD simulations can accurately simulate blood flow in veins and arteries. CFD also permits the inclusion of various blood flow conditions in 3D models, allowing the simulation of different types of arterial diseases. Referring now to FIG. 4, shown therein is an example of CFD using a realistic arterial geometry and a realistic velocity field.

To take advantage of the accuracy of CFD techniques without sacrificing the possibility real-time performance, CFD information may be pre-computed in the form of particle trajectories. Particle trajectories are a way of encoding CFD velocity field information, as illustrated in FIG. 4. Each particle trajectory is divided in space and time; therefore it will suffice to select a specific point within each particle trajectory that will be associated with a particular point scatterer. Point scatterers can be assigned CFD information for a given time interval which will correspond to a "Frame" or snapshot of the flow field in a given time instant. This time interval will be chosen according to the maximum desired pulse repetition frequency (PRF). For a PRF lower than the maximum, it is possible to use the same dataset just by skipping interleaved frames according to the desired PRF. Accordingly, only PRFs which are an integer multiple from the maximum can be successfully reproduced using the original dataset. Thus, particle trajectories can be pre-computed from CFD data for 3D models, allowing the particle trajectories to be quickly retrieved by the module 110 from the database 101 when generating ultrasound images. To relax the assumption that only integer multiples of the maximum PRF can be selected, an alternative approach is to assume that the particle trajectories were built with enough resolution according to specific flow conditions for a given situation. Then, point scatterers are chosen from these particle trajectories according to the sample volume location and its corresponding time in the cardiac cycle. Any suitable know interpolation algorithm can be used to fill up the gaps of those trajectories that are crossing the sample volume but for which there is no information at the specific point in time required for the simulation process.

In this manner, CFD information can be incorporated into the ultrasound imaging simulation, allowing the possible simulation of spectral Doppler mode, color Doppler mode, and power Doppler mode ultrasound images. For example, the added information from the CFD simulations makes it possible to generate a characteristic spectrogram plot curve from which blood flow velocity information can be measured, so the operator can assess the degree of the disease in a specific region. In addition, other important parameters can be measured from this spectrogram plot curve, including the pulsatility or the resistance indexes. Combining ultrasound and blood flow physics modeling thus provides a simulation that more closely mirrors reality.

Figure 5B:
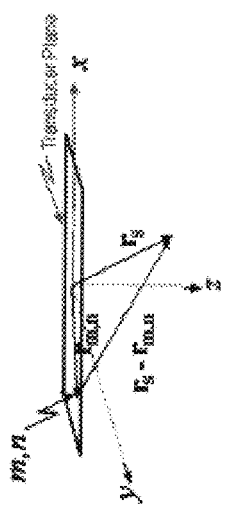
FIG. 5B illustrates vectors defining locations of a point source and a scatterer according to a method of generating a radio-frequency signal for use in simulating an ultrasound image.
Figure 5A:
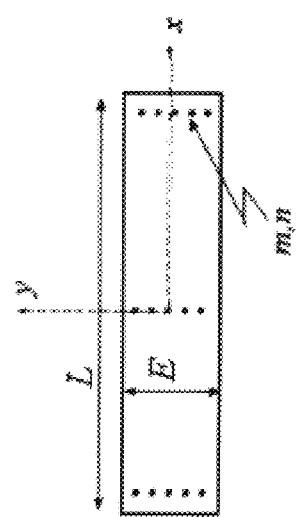
FIG. 5A illustrates the geometric definitions for a point source array according to a method of generating a radio-frequency signal for use in simulating an ultrasound image.
Figure 5C:
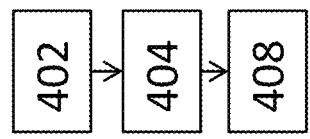
FIG. 5C is a flowchart illustrating a method of generating a radio-frequency signal for use in simulating an ultrasound image.

Referring now to FIGS. 5A to 5C, the steps of a method 400 will now be described. FIG. 5C is a flowchart of a method 400. Method 400 generally provides additional detail regarding the computational steps performed in relation to method 300 for generating an RF signal. Referring specifically to FIGS. 5A to 5B, shown therein are geometric definitions of a modeled point-source array. FIG. 5A illustrates array dimensions and locations of point sources that may be used to simulate transmit/receive behaviour. FIG. 5B illustrates vector definition of the locations of one point source and the position of a scatterer.

As in method 300 above, point sources associated with a transducer, and point scatterers associated with a 3D model of an organ, are modeled in the same coordinate system. Within each 3D model of an organ, point scatterers are randomly distributed. A field of view of the transducer is the intersection of the transducer's modeled acoustic field and the point scatterers for a given 3D model (organ phantom). During simulation, at any given time, each scatterer is associated with a given scatterer amplitude (reflection coefficient) for a given tissue within which each scatterer is located. The scatterers' spatial positions are used to determine impulse response.

The methods 300, 400 generally provide point source methods of representing the ultrasound wave output of an ultrasound transducer. A point source method allows the representation of the approximate radiation characteristics of a complex source of radiation, by a plurality of point sources. For example, Ahmad et al. used this approach in studying how suitably phased point sources could be used to represent the frequency domain radiation characteristics of simple planar phased arrays. See particularly, Ahmad R, Kundu T, Placko D., *Modeling of phased array transducers*. The Journal of the Acoustical Society of America. 2005; 117(4):1762-1776.

At block 402, the position of point sources of an illustrative sham transducer are defined for a simulation, provided a phased array whose dimensions are L and E in the lateral and elevation directions as illustrated in FIG. 5A, and assuming that M and N point sources/receivers are used in the elevation and lateral direction to represent the T/R field response. The positions of point sources can be determined by assuming that each point source corresponds to the same incremental area of $\Delta A = EL/(MN)$. If M and N are odd then a given point source/receiver can be referenced with respect to the center of the array by the index m, where $m = -(M-1)/2 \ldots 0 \ldots (M-1)/2$ and $n = -(N-1)/2 \ldots (N-1)/2$. Other embodiments of the array are contemplated, depending on the shape of a modeled sham transducer.

At block 404, for a given simulated transmission from the point sources, transmit time delay, transmit velocity potential and delayed and apodized impulse response are computed.

When transmitting, it can be assumed that the lateral focal point lies on the plane y=0 at the point $(x_L, 0, z_L)$. The elevation mode focus produced by a cylindrical lens is taken to be at the point $(0, E, Z_E)$. To achieve these focal points, FIG. 5B shows that the transmit time delay for element m, n, where c is the speed of sound can be written as $$\tau_{m,n} = \frac{1}{c}\left[\sqrt{\lambda_E^2 + \left(\frac{E(M-1)}{2M}\right)^2} - \sqrt{\lambda_E^2 + \left(\frac{mE}{M}\right)^2} + \sqrt{\lambda_L^2 + \left(\frac{L(N-1)}{2N} - x_L\right)^2} - \sqrt{\lambda_L^2 + \left(\frac{nL}{N} - z_L\right)^2}\right] \quad (1)$$

Thus, for a scatterer at $r_s=(x_s, y_s, z_s)$, the transit time from element m, n to the scatterer is $$t_{m,n}^B = \frac{r_{m,n}^s}{c} = \frac{1}{c}\sqrt{[x_s - nL/N]^2 + [y_s - mE/M]^2 + z_s^2} \quad (2)$$

The transmit velocity potential response at the scatterer due to a surface velocity impulse at the point source m, n is proportional to $$h_{m,n}^T(t, r_s) = \delta\left[t - \frac{r_{m,n}^s}{c}\right]\frac{e^{-\alpha r_{m,n}^s}}{r_{m,n}^3} \quad (3)$$

where α is the attenuation of the propagation medium, which is momentarily assumed to be frequency independent and equal to that at the center frequency. The impulse applied to point source m, n should be delayed by $T_{m,n}$, as given by formula (1), so that the delayed and apodized impulse response at the scatterer is given by $$h_{m,n}^T(t - \tau_{m,n}, r_s) = A_n \delta\left[t - \tau_{m,n} - \frac{r_{m,n}^s}{c}\right]\frac{e^{-\alpha r_{m,n}^s}}{r_{m,n}^s} \quad (4)$$

where the apodization (assumed to be independent of y) is incorporated in $A_n$ which also includes any constants.

At block 406, by summing the impulse responses from all point sources to the scatterer, the resulting transmit impulse response is given by $$h^T(t, r_s) = \sum_{m=-(M-1)/2}^{(M-1)/2} \sum_{n=-(N-1)/2}^{(N-1)/2} A_n \delta\left[t - \tau_{m,n} - \frac{r_{m,n}^s}{c}\right]\frac{e^{-\alpha r_{m,n}^s}}{r_{m,n}^s} \quad (5)$$

If the transducer surface velocity waveform resulting from a voltage waveform applied to the transducer is given by $v^E(t)$, and it is assumed that the transducer electromechanical transfer function is unity, then the pressure waveform seen by the scatterer will be proportional to the convolution $$\frac{\partial v^E(t)}{\partial t} * h^T(t, r_s).$$

Since each scatterer is assumed to behave as a point source whose radiation is detected by the M, N point receivers, it follows from reciprocity, that the T/R impulse response for a single scatterer at $r_3$ is of the form $$h^{TR}(t,r_s) = h^T(t,r_s) * h^R(t,r_s) \quad (6)$$

in which $h^R(t, r_s) = h^T(t, r_s)$.

At block 408, for S scatterers the overall T/R impulse response can be expressed as $$h_S^{TR}(t, \tau) = \sum_{m=1}^{S} h^T(t, r_s) * h^T(t, r_s) \quad (7)$$

In brief, methods 300, 400 assume that the transducer is exactly the same in transmission and in reception; in consequence it is only needed to compute the "one way impulse response" and then equation (6) is used to compute the spatial impulse response for a single scatterer and all point sources. Equation (7) shows how to compute the total impulse response for all scatterers.

The effects of frequency-dependent attenuation can be approximately accounted for in a similar manner to that used in Field II, as described in *Ultrasound fields in an attenuating medium*, Jensen J A, Gandhi D, O'Brien Jr W D, Ultrasonic Symposium, 1993, proceedings, IEEE 1993. IEEE; 1993, p. 943-946. This is especially important when B-mode images are formed using wideband transmit signals in order to obtain good spatial resolution.

The basis of method 400 is a causal minimum phase impulse response expression that assumes that attenuation consists of two terms: one being frequency independent the other being a linearized frequency dependent term, i.e., $\alpha(f)=\alpha_o+\alpha_L(f-f_o)$, where $\alpha_o$ is the center frequency attenuation, $\alpha_L$ characterizes the linear dependence and f is expressed in MHz. The frequency independent term is accounted for by the exponential term in equation (3). The linearized frequency dependent term can be included in the convolution by assuming a linear change in attenuation at the center frequency and taking the distance as the mean distance to the aperture as described in the Field II manual.

Method 400 could be implemented for simulations to determine spectral Doppler flow and B-mode images. For B-mode images a phantom with a volume of scatterers could be implemented with the parameters listed in Table 1 below, and as described in *Computer phantoms for simulating ultrasound B-mode and cfm images*, Jensen J A, Munk P., Acoustical Imaging, Springer, 1997, p. 75-80 and as described in *Fast and Mechanistic Ultrasound Simulation Using a Point Source/Receiver Approach*, Aguilar L A, Cobbold R S, Steinman D A, IEEE Transactions on Ultrasonics, Ferroelectrics and Frequency Control, 2013, 60(11): 2335-2346.

TABLE 1

Illustrative Parameters for use in Simulated Ultrasound Imaging

| Parameter | Spectral Doppler | B-mode |
| --- | --- | --- |
| Active elements | 16 | 64 |
| Imaging elements | N/A | 192 |

TABLE 1-continued

Illustrative Parameters for use in Simulated Ultrasound Imaging

| Parameter | Spectral Doppler | B-mode |
|---|---|---|
| Lateral width | 0.29 mm | 0.29 mm |
| Elevation height | 5.0 mm | 5.0 mm |
| Kerf | 0.027 mm | 0.05 mm |
| Elevation lens focus | 14.0 mm | 20.0 mm |
| Lateral focal point | 40.0 mm | 60.0 mm |
| Lateral F-number, $F_N$ | 2 | 1.5 |
| Center frequency, $f_o$ | 5.0 MHZ | 5.0 MHz |
| Apodization | None | None |
| Atten. at $f_o$ | 40.28 Np/m | 40.28 Np/m |
| Freq. dep. Attn, $f_L$ | 0 | 2.47 Np/(m · Mhz) |
| Speed of sound | 1540 m/s | 1540 m/s |

For a spectral Doppler, pulsatile (Womersley) flow could be simulated with a pulse-repetition frequency of 15 kHz, a narrowband 9-cycle Hanning-modulated sine wave, and a Doppler angle of 30°. The pulsatile flow waveform could be approximately that of the femoral artery and could have a time-averaged mean flow velocity of 0.15 m/s. Flow studies could assume an 8.4 mm inner diameter flow tube, roughly corresponding to a typical femoral artery, and a fluid could be seeded with 1000 point scatterers, randomly distributed over an entire 2.772 mm length of the flow tube encompassing the focal region, providing a scatterer density of 6.5 scatterers/mm³. To enable the spectral Doppler signal to be obtained over one period of the waveform (1.0 s), scatterers that exit the seeded tube length could be recycled either to the input or the output depending on flow direction at a particular time.

Computation time for effectuating the simulation described above may be minimized by varying computational implementation. The computations described in relation to methods 300, 400 can be implemented on multiple processors, such as on cores of a multiple-core processor or graphics processing units (GPUs), in order to decrease computing time. For example, each core can provide calculations for a single point source. Additionally, the methods can take advantage of code vectorization. Modern microprocessors have vectorised units, which operate on one-dimensional arrays of data vectors per clock cycle. This is in contrast to scalar processors, whose instructions operate on single data items. Because the methods represent the transducer model using (independent) point sources, this representation is optimal to take advantage of vectorised units, which may substantially increase the computational performance of the simulation. By storing a set of point sources and a set of point scatterers in vectorised units, multiple operations can be computed in the same amount of time as one operation without using vectorization units. Additionally, owing to its simple representation of the transducer model and the organs, the methods are amenable to be ported to a GPU platform.

In the following paragraphs, methods will be described which may increase the computational performance of the methods 300, 400 and associated post-processing for different ultrasound modes.

Figure 6A:
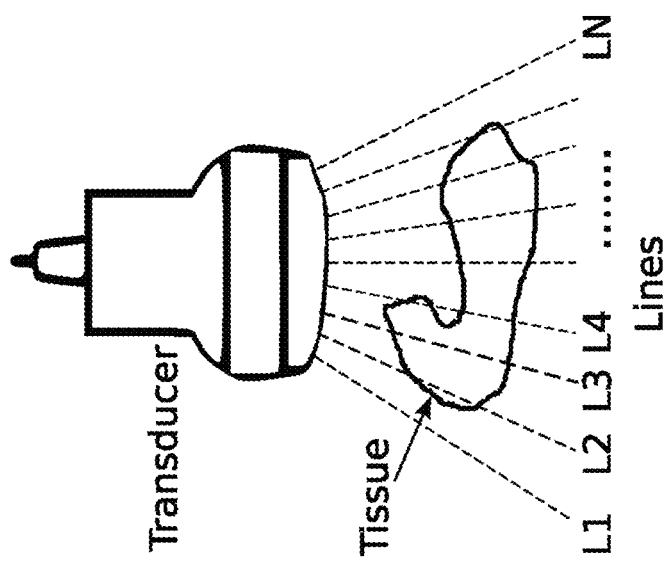
FIG. 6A illustrates an ultrasound transducer and its associated transducer lines.
Figure 6B:
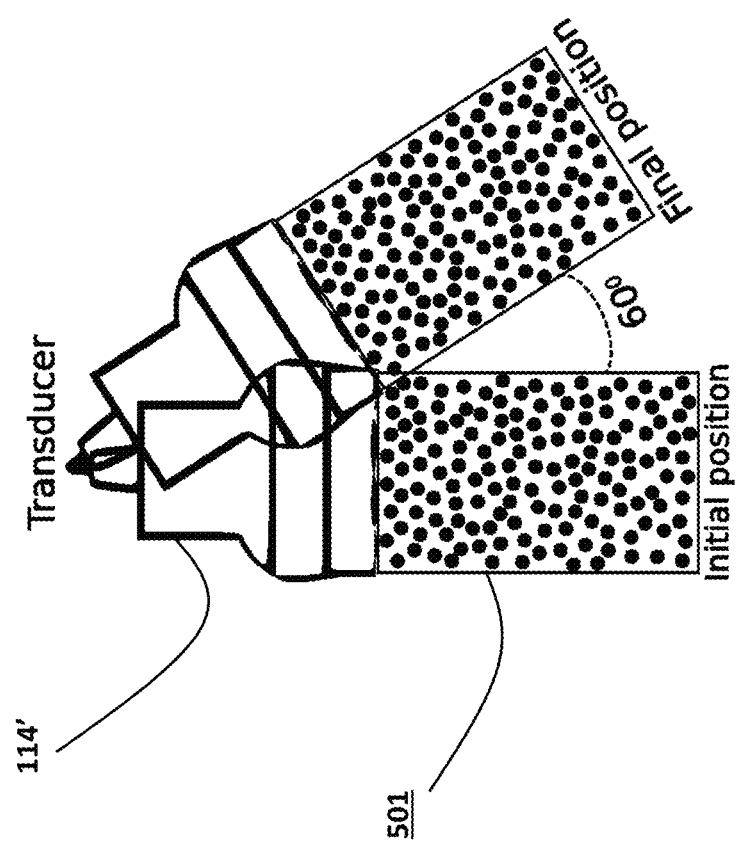
FIG. 6B illustrates a simulated ultrasound transducer and a spatially invariant volume of scatterers.
Figure 7:
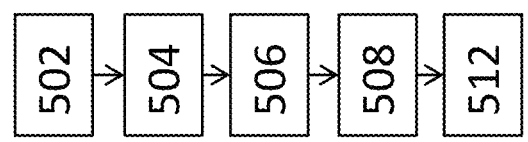
FIG. 7 is a flowchart illustrating a method of generating a B-mode image.

Referring now to FIGS. 6A, 6B and 7, for B-mode imaging, providing a spatially invariant field of view for the simulated transducer may increase performance of the simulation.

In a real-ultrasound system and in the simulation model described herein, the transducer concentrates its energy in the acoustic irradiation direction, in an axial direction in front of the transducer probe. To cover the complete field of view (a defined volume located in front of the transducer for a specified axial distance) a subset of transducer elements are activated at a given time, irradiating a partial region (known as a line), as shown in FIG. 6A. Then, another subset adjacent to the previous one is activated to form another line. The same procedure is followed until the whole field of view is covered. A B-mode image is a representation of the different types of tissue encountered by all transducer lines combined. Each tissue has different properties. Some tissue (e.g. bone) reflects a greater amount of the irradiated ultrasound energy. Other types of tissue reflect less energy (e.g. muscle). In the case of a simulation, each 3D model comprises a large number of discrete point scatterers to represent tissue. In a simulation, there are thus two variables that play a major role in the B-mode image generation process: the scatterer positions (which represent the tissue) with respect to the transducer position, and the scatterer amplitude which varies depending on the reflectivity of the type of tissue within which a scatterer is positioned. The classic gray scale tone assigned to a B-mode image is proportional to the characteristics of the underlying tissue properties.

According to a method 500 depicted in FIG. 7, at block 502, a fixed volume of scatterers 501 (such as approximately one scatterer per quarter wavelength of an ultrasound wave) are modeled to be randomly distributed across the field of view of the representation of a sham transducer 114'. According to the method 500, these scatterers 501 are assumed to be fixed at their corresponding spatial positions with respect to the simulated transducer model. By providing that the scatterers are spatially invariant, it is no longer necessary to re-compute the spatial positions of the scatterers (and associated impulse responses) when the modeled transducer changes its position (unless the parameters of the transducer change). A representation of this is illustrated in FIG. 6B, where the transducer 114' has been rotated 60 degrees, however the relative position of the scatterers 501 with respect to the transducer is exactly the same as the previous position.

The assumption that the fixed volume of scatterers 501 is fixed relative to the transducer 114' makes it possible at block 504 to pre-compute the impulse response for all the scatterers within the scatterer volume 501, which otherwise have to be computed during simulation at great computational effort every time the impulse response for a number of scatterers has to be determined. Furthermore, since the reconstruction of the ultrasound image can be more sensitive to signal phase than amplitude, further performance and storage gains may be achieved by pre-computing and storing the phases (which are scalar values) on a finer grid compared to the (unaligned) impulse response (which is a vector array). The computational cost associated with this pre-computation during simulation is merely the amount of memory used to store the pre-computed impulse responses for all scatterers that comprise the field of view of a transducer plus the final summation of the individual impulse responses from each scatterer that will be multiplied by the characteristic tissue amplitude factor during simulation, as described below.

In order to generate a B-mode image, at block 506, the associated scatterer amplitude factor for each scatterer needs to be determined. This amplitude is a property associated with each scatterer for a given position of the scatterer in a 3D model, and is represented by a scalar value that indicates the strength of a signal reflected by each scatterer. This scatterer amplitude is thus dependent on the type of tissue in which a scatterer is located at a particular time. It is possible to efficiently recover these amplitudes from all scatterers and use them to scale the pre-computed impulse responses. To effect this, it is required to find the intersection of the scatterers that form the fixed volume with the scatterers from the 3D models that forms the organs. This intersection can be found by calculating the nearest scatterer of a given organ and assigning its amplitude value to a corresponding scatterer. In other words, for a given scatterer in the fixed volume of scatterers, a scatterer in the 3D model is identified having a minimum distance therefrom, and its associated scatterer amplitude is assumed by the scatterer in the fixed volume of scatterers. This process can be efficiently done by using one of the nearest neighbor approximation methods as described in Marius Muja and David G. Lowe: "Scalable Nearest Neighbor Algorithms for High Dimensional Data". Pattern Analysis and Machine Intelligence (PAMI), Vol. 36, 2014.

If the transducer changes position it is necessary, at block 508, to interpolate onto the fixed scatterers the updated properties for the scatterers for their new positions in the 3D model of an ultrasound target.

Figure 8B:
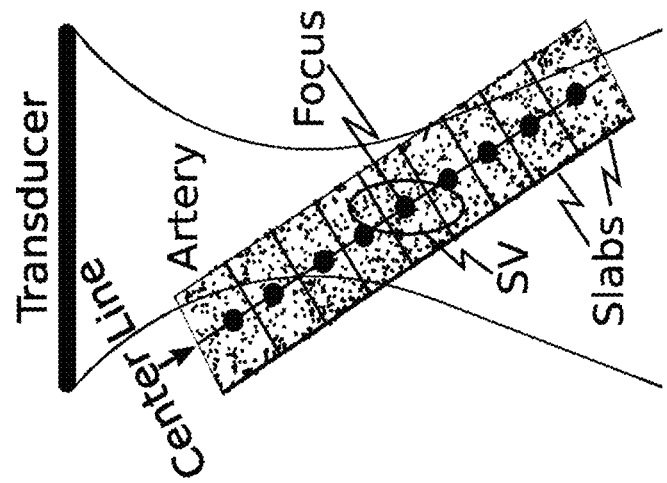
FIG. 8B illustrates the field of view of a simulated transducer according to a method of segmenting the geometry of an ultrasound target model.
Figure 8A:
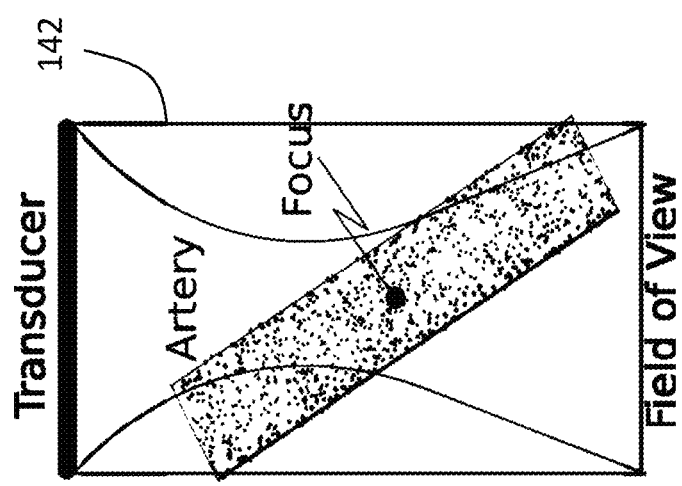
FIG. 8A illustrates the field of view of a simulated transducer.
Figure 8C:
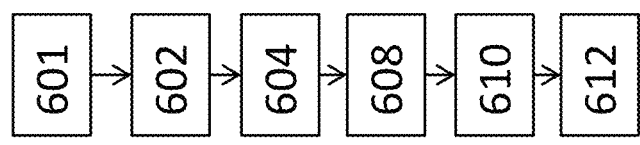
FIG. 8C is a method of segmenting the geometry of an ultrasound target model.

Referring now to FIGS. 8A to 8C, a method 600 of segmenting scatterers in an ultrasound target is provided which may increase simulation performance for some types of imaging, such as for Spectral Doppler mode imaging. FIG. 8A illustrates scatterers as black dots and provides a 2D representation of the field of view of a transducer. FIG. 8B illustrates a sample volume and segmentation of the geometry of an ultrasound target model to improve simulation performance. FIG. 8C provides a flowchart of blocks relating to the method 600.

To simulate spectral Doppler mode, it is required to simulate blood flow. To this end, a number of sets of scatterers have to be analyzed. The number of sets depends of the PRF (Pulse Repetition Frequency) variable. Typically, the PRF is between 1 KHz and 20 KHz. This means that it is required between 1000 to 20000 sets of scatterers to simulate a complete cardiac, cycle which lasts about 1 second. Each set is composed of a number of scatterers and each set corresponds to a specific time point within the cardiac cycle. Each set of scatterers is random and uniformly distributed so they occupy the whole arterial geometry, denoted in FIG. 8A as black dots. Each individual set provides a snapshot of the whole data set and for each individual set it is necessary to compute the radio frequency RF-signal. The RF-signal is thus computed for the intersection of the field of view (outer rectangle 142 in FIG. 8A) and each individual set of scatterers, which may be spread throughout the whole geometry. For example, assuming that each individual set comprises 5000 scatterers spread across the whole artery for a PRF of 15 KHz, the ultrasound simulation method has to process: 5000×15000=75,000,000 scatterers in about 1 sec. Even utilizing multiprocessing and vectorization techniques, and even if the whole dataset of scatterers and their corresponding positions are pre-computed, the computational burden may still be too high for approximately real time rendering of ultrasound spectrogram.

A method 600 is thus provided that may reduce the computational burden by ensuring that only the scatterers that contribute the most to the generation of the Doppler signal are computed. According to the method, only scatterers located inside of a sample volume (SV) region are considered, while the rest are discarded, instead of considering all scatterers within the geometry for all time points. At block 601, the SV is defined as the spatial location where most of the acoustic energy is concentrated by the transducer, illustrated by an ellipse and labeled in FIG. 8B. The center of the SV is defined as the focal zone or focus of the transducer geometry (as labeled in FIGS. 8A and 8B). The SV is dynamic because its position varies according to changing transducer position and orientation, or according to changing transducer parameters (e.g. parameters to re-locate the focal zone by changing the transducer delays).

In the described ultrasound simulation, it is enough to provide the spatial coordinates of the focal zone and the delays will be adjusted accordingly. More particularly, as described above with regard to block 404, to compute the corresponding delay for a given point source, it is sufficient to define a single spatial position (focal zone/point) and then apply formula (1) to compute the corresponding delay for that point source.

For carrying out a simulation according to the method 600, it is required to identify which scatterers are within the SV for all time points. To do so, at block 602, the geometry of the 3D modeled ultrasound target can first be broken down into a plurality of regions. For example, the geometrical center line of a 3D model can be used to divide the vessel geometry into a number of equidistant and contiguous regions that referred to hereafter as slabs. FIG. 8B illustrates the center line and the slabs that divide the geometry all along the center line. Each slab may be assigned an identification number. At block 604, for all scatterers in every set and for all time points, the minimum distance from each scatterer to all slabs is calculated. At block 606, the corresponding number of a slab that is closest to each scatterer is identified and assigned to that scatterer. Accordingly, all scatterers will be assigned a unique slab number (i.e., of their closest slab). At block 608, one or more contiguous slabs are selected that will contain the whole SV region as shown in FIG. 8B. Because the focus location was defined at block 601, the slabs can be determined that contain only the focus, or contain the focus and the SV. It will be understood that the focus can be defined as a single spatial location, while the SV is region could extent to more than one slab. At block 610, once that slab(s) is(are) identified that contain the focus and SV, it is required to determine the scatterers that are part of the identified slab. Every set of scatterers may thus be sorted according to its previously determined slab number.

It will thus be understood that the scatterers are spatially grouped in clusters in the memory of the computer (adjacent slabs are spatial neighbors), which facilitates use of fast search algorithms (e.g. binary search) to sort scatterers according to their slab numbers. Determining which scatterers belong to a given spatial region is transformed into a straightforward process of searching which slab is closest to the focus, which considerably reduces the size of the domain (number of scatterers to include in the simulation). It may also help to reduce cache misses while increasing the locality of the data which in consequence increases the computational performance of the simulation. Assigning a slab number to each scatterer and the associated sorting of the slabs may be done as a pre-processing step, previous to the spectrogram calculation, to minimize computational burden.

A spectrogram can thus be computed from a relatively small region, the SV region, where most of the ultrasound energy is concentrated. Rather than defining the SV as an ellipsoid (as illustrated in FIG. 8B), the SV may be approximated using a convex hull which may be a close representation of the SV region and whose shape is observed in FIG. 9B. The SV region may thus be defined using a threshold criterion with respect to the maximum power, such as a −20 dB threshold. It may be assumed that scatterers that have a value less than the threshold will not significantly contribute to the spectrogram. To narrow down the simulation domain and take into account only those scatterers above the threshold, it is necessary to determine which scatterers belong to the SV region according to the threshold. As described above, a first step may be to find which slab contains the focal zone, then, it has to be decided if more slabs will be included so the SV will be totally contained within those slabs. Because adjacent slabs group spatially located scatterers, it is assured that the SV region is within this group. More specifically, observing FIG. 8B, it can be seen that the sample volume region (SV, the ellipse) is included within more than one slab, in this case we can observe that three slabs totally contain the SV. These three slabs are spatially grouped according to the geometrical center line. It also happens that they are contiguous in the memory of the computer.

A method to identify which scatterers totally contain the SV region is to compute the convex hull for the threshold criterion, the convex hull being described in Barber, C. B.; Dobkin, D. P.; and Huhdanpaa, H. T. "The Quickhull Algorithm for Convex Hulls." ACM Trans. Mathematical Software 22, 469-483, 1996. The convex hull of a set of scatterers "S" is the smallest convex polygon that contains all the points of S, as shown in FIG. 9B. More specifically, FIG. 9B illustrates the convex hull that contains the sample volume represented by the red dots for lateral and elevation views. The method thus determines which scatterers from the selected group of slabs are within the convex hull to guarantee the minimum possible set of scatterers that forms the SV region. The convex hull can be pre-computed once the SV region location is set (red ellipse in FIG. 9A), then the convex hull is fixed and can be used for all subsequent calculations until a new SV location is chosen.

According to an alternate mode used by the system 100, if the quantity of point scatterers that comprises a given organ is high, increasing computational burden, rather than discretizing the 3D model with point scatterers, the 3D model's original surface mesh can be used. In this way, the surface mesh will be defined with a range of reflection coefficient values that will be randomly and dynamically assigned accordingly to the type of tissue. In this way, it will suffice to assign a corresponding value within the range of values assigned to this particular tissue, to the scatterers that compose the fixed volume in 501. In the same manner as the method 500, it is required to find the intersection with the surface mesh and the scatterers of the fixed volume. For this end, instead of using the Nearest Neighbor Algorithms other computational geometry methods have to be used to find out when a point scatter is spatially located within a 3D surface. To do so, there are different techniques. Among them, the ray-tracing method is one of the best candidates because its simplicity and its amenability to be implemented via GPUs. By using GPUs to perform some of the most computationally intensive parts of the ultrasound simulation method, performance can be slightly increased in some scenarios. Details of this and other methods are described in Joseph O'Rourke, "Segment-Triangle Intersection" in Computational Geometry in C, 2nd Edition, 1998.

In this alternative method, system dependent artifacts commonly found in a real ultrasound system, for example speckle, spectral broadening, etc. can be modelled and simulated. Further, the system 100 may be computationally capable of modelling anatomical context, such as surrounding organs, muscle, bone, fat, cartilage, etc., which improves the realism of ultrasound artifact simulation using 3D organ models. The inclusion of anatomical context substantially increases the computational demand of the simulation process.

In addition, it can be desirable to present other key artifacts via the system to improve realism. For example, shadowing artifacts that arise in the presence of bone or calcified interfaces can absorb and attenuate the ultrasound beam. Refraction artifacts caused by the difference in refraction indices between two different types of tissue impact the resulting images. These tissue-structure artifacts depend on the tissue structure, composition, and behaviour in the presence of an ultrasound field. It is desirable to include such tissue-structure artifacts and to account for the interaction among scatterers in the ultrasound images generated by the system for ultrasound simulation.

Figure 10:
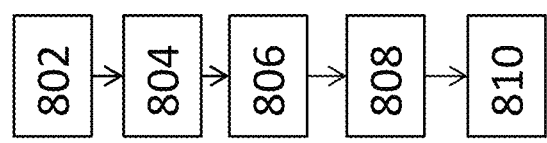
FIG. 10 is a flowchart illustrating a method for simulating ultrasound in accordance with another embodiment.

The general method 800 used by the system 100 for ultrasound simulation using surface meshes is shown in FIG. 10. The distances (phases) from all point sources to all scatterers is determined (802). Next, the impulse response for a given scatterer and all point sources is computed (804) The system 100 then convolutes the impulse response with itself to obtain the backscatterer impulse response (806). Then all impulse responses are summed (808). Finally, the system 100 convolutes the total signal with the excitation pulse to obtain the RF-signal (810).

The distance determinations 802 and computing of the impulse responses 804 is performed in the system by the GPU. An example of a suitable GPU that can be implemented in system 100 is a NVIDIA™ GeForce™ 980 m, equipped with 1536 discrete processors. It has been found that, by shifting these tasks to the GPU, significant performance gains can be achieved. Linearization of the main data structures enables them to be more naturally mapped out to the grid layout arrangement suitable for numerous GPU processors. In this way, memory latency, a main source of bottlenecking in GPU processing, is substantially minimized. For the convolution at 806, the impulse responses may be transformed by the system 100 into the frequency domain, for example to take advantage of a fine-tuned GPU-based FFT library. The summation of the many convoluted signals at 808 is done by adapting the parallel prefix sum algorithm, initially described in Ladner, R. E.; Fischer, M. J. "Parallel Prefix Computation", Journal of the ACM 27 (4): 831-838, 1980 and more recently ported to the GPU as described in Sengupta, Shubhabrata; Harris, Mark; Zhang, Yao; Owens, John D., "Scan primitives for GPU computing", Proc. 22nd ACM SIGGRAPH/EUROGRAPHICS Symposium on Graphics Hardware, pp. 97-106, 2007.

Figure 11A:
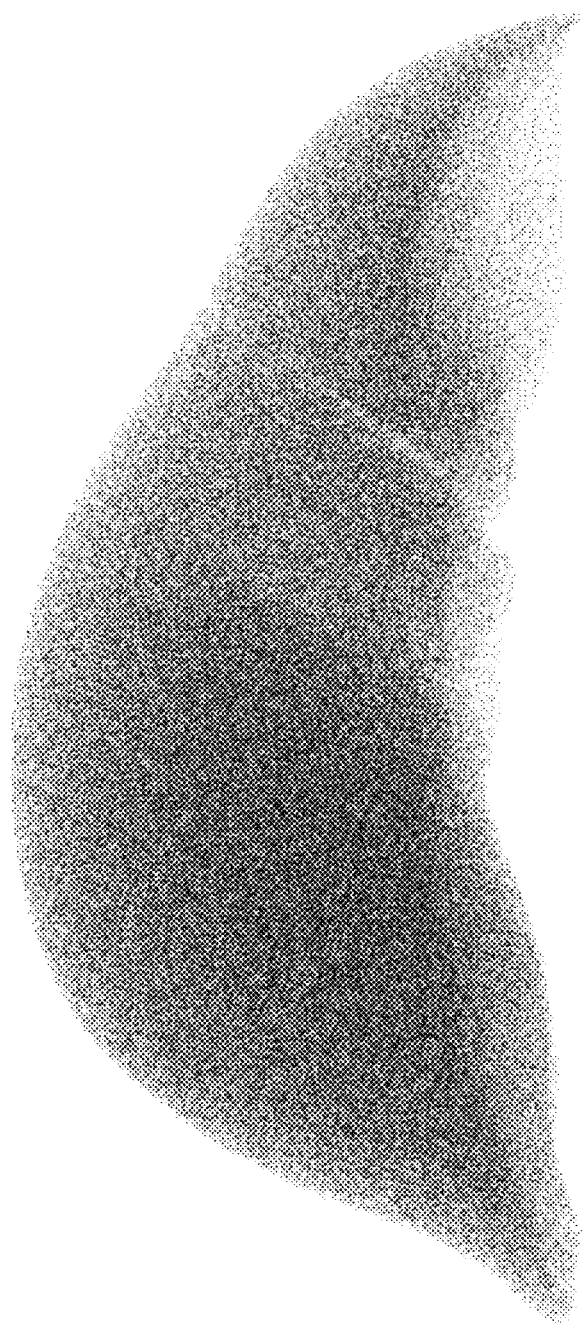
FIG. 11A illustrates a point scatterer model of a liver used by the system for simulating ultrasound imaging using the method illustrated in FIG. 7.

In a real ultrasound study, a sonographer evaluates the subject's described condition by positioning the probe within the nominal region of interest. The operator typically finds the organ of interest based not only in its appearance, but also guided by the adjacent organs and tissue. FIG. 11D shows a real ultrasound image, with the liver among other anatomical structures like the gallbladder, the aorta, the inferior vena cava, liver ligaments, and a section of the diaphragm at the top. From the ultrasound image, it is possible to discriminate the different structures due to the characteristic reflectivity properties of the different types of tissue.

Figure 11B:
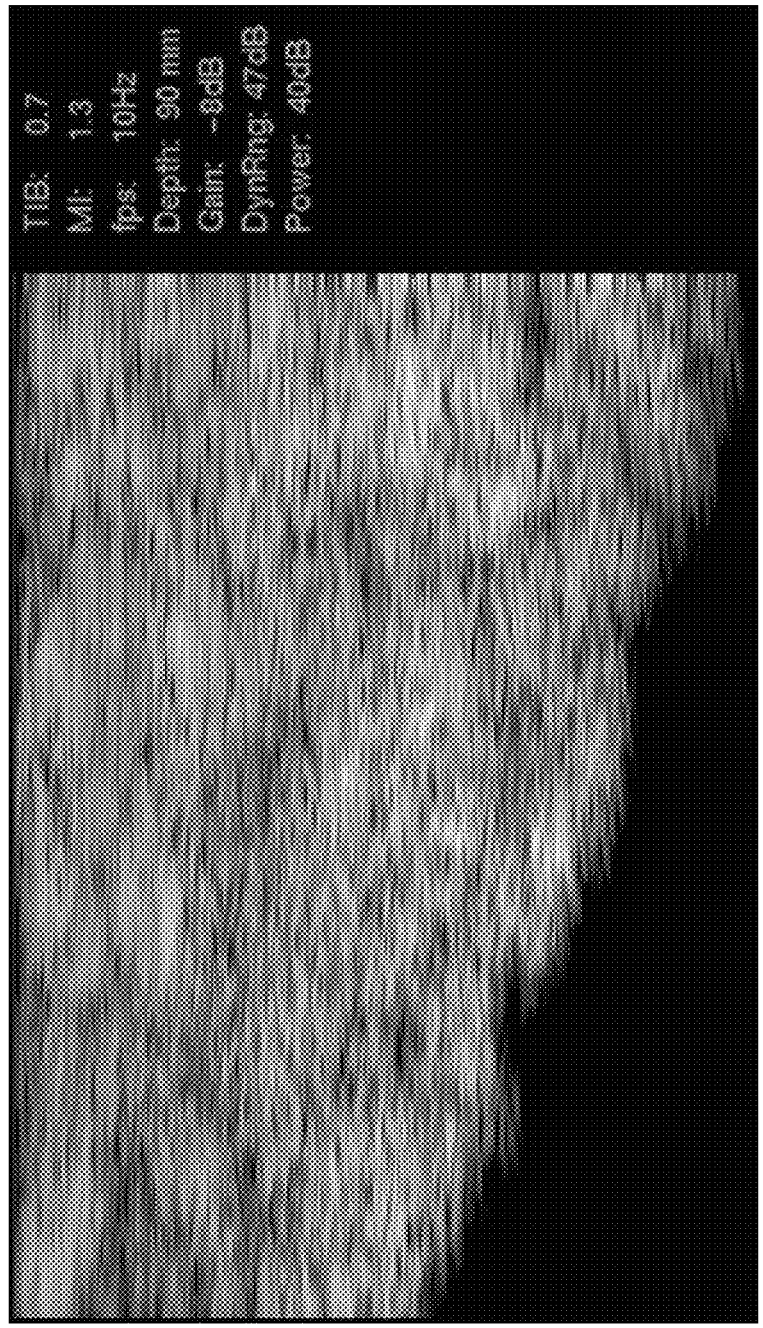
FIG. 11B illustrates an image generated by the system for simulating ultrasound imaging storing the point scatterer model of FIG. 11A.

FIG. 11B is an exemplary simulated ultrasound image produced using the scatterer approach. The simulated ultrasound image shows an isolated "organ-in-a-box". The system 100 seeds a large number of scatterers volumetrically, with sufficient density to describe the organ shape, and with variable backscatter properties to model organ inhomogeneities. An example of such a model is shown for a liver in FIG. 11A.

Figure 11C:
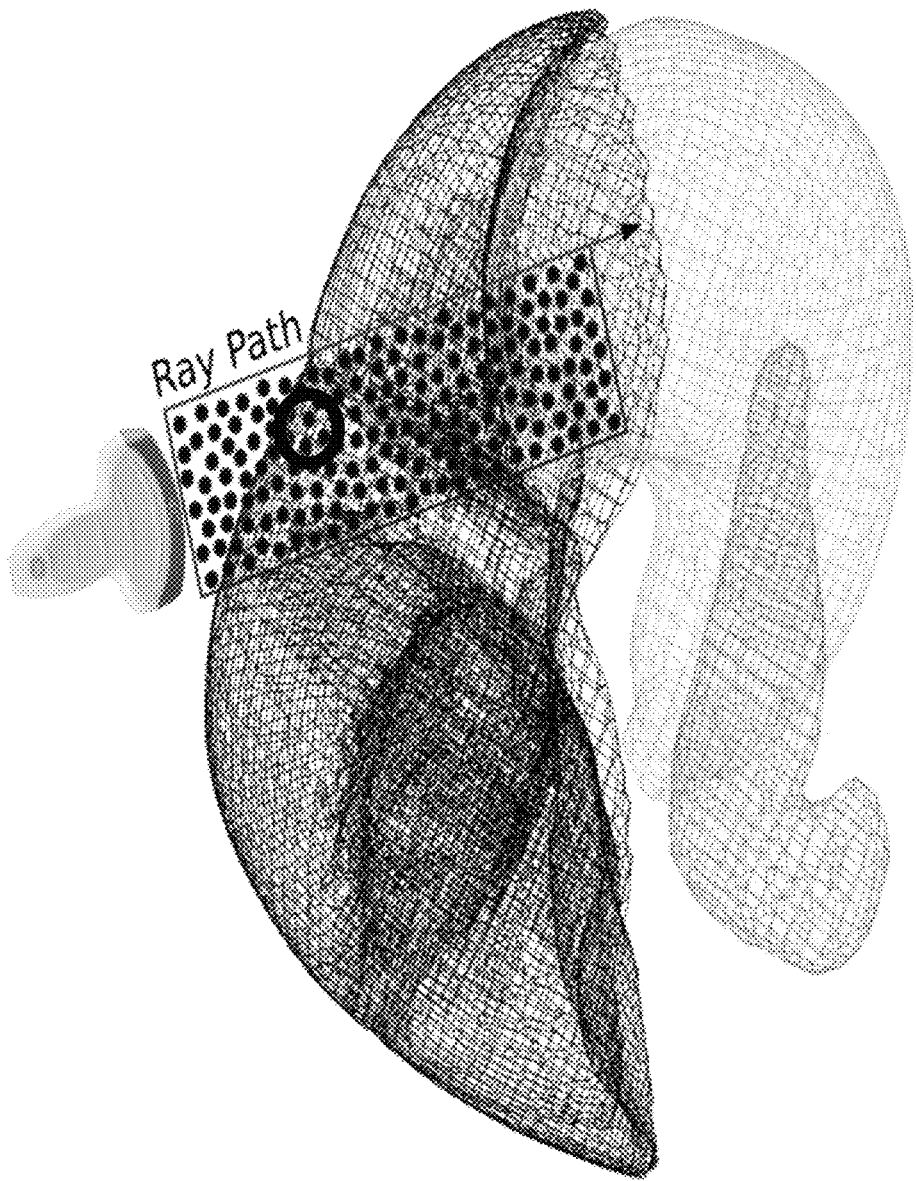
FIG. 11C illustrates a triangulated surface mesh model of the liver of FIG. 11A and adjacent organs, as well as ray tracing for modeling ultrasound beams.
Figure 11D:
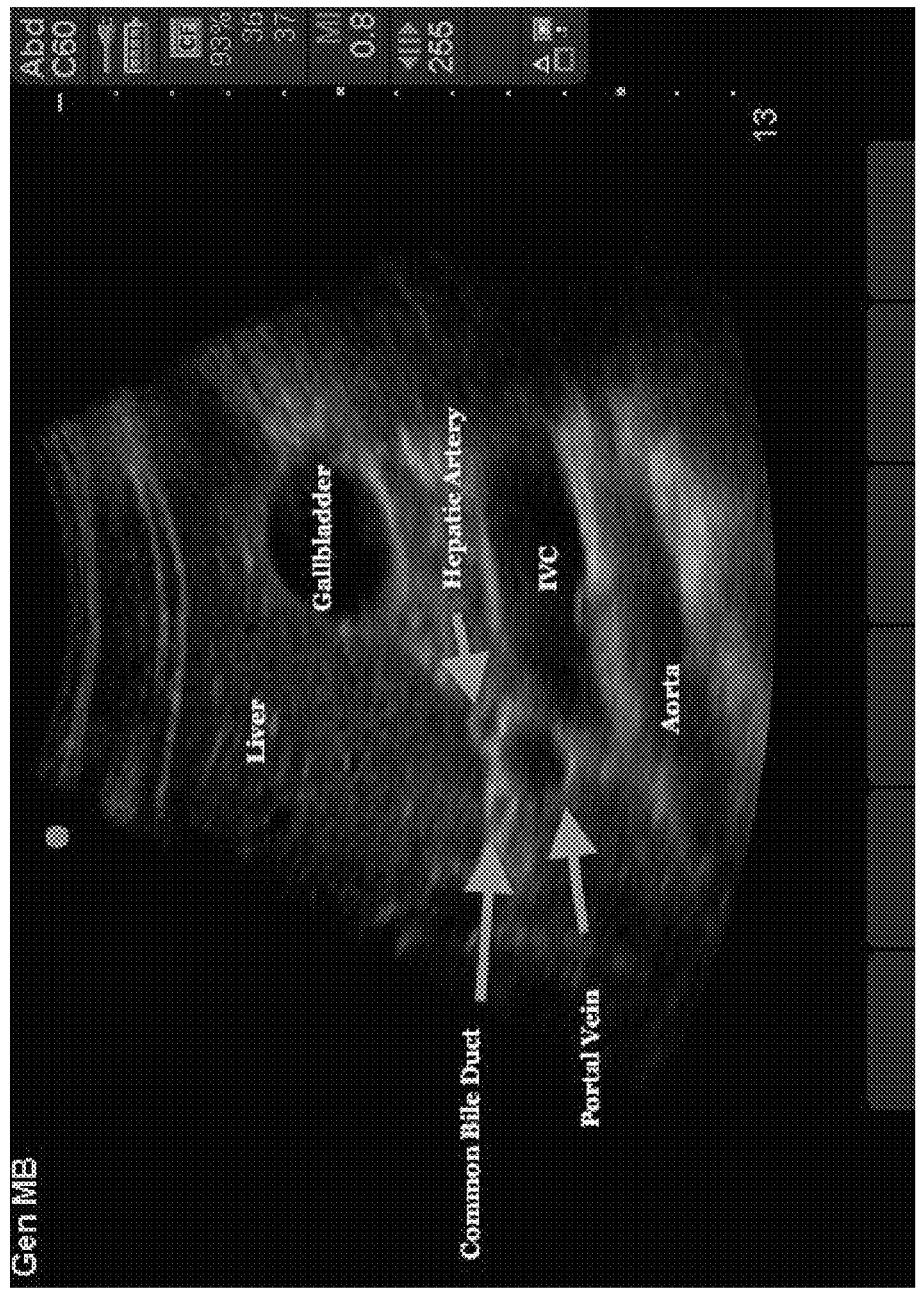
FIG. 11D illustrates a real ultrasound image with the liver among other anatomical structures.

An equivalent 3D triangulated surface mesh of every organ/tissue model produced by the system 100 in the surface mesh mode is shown in FIG. 11C. These 3D triangulated mesh models are stored in the database 101.

The system 100 identifies the organ/tissue surface within which each transducer-fixed scatterer point is currently located (e.g., circle in FIG. 11C). By doing this, the number of scatterers that have to be interrogated, the storage requirements, and the computational requirements can substantially reduced in some scenarios. The triangulated meshes are the original format of the models, and an additional advantage of representing models with triangulated meshes is that GPUs were designed to process this kind of data structure. The system can implement techniques such as collision detection and barycentric based mesh intersection algorithms to map, on the fly, scatterer points to organ/tissue volumes.

Some of the main challenges in an ultrasound examination are the ability to accurately discriminate real anatomical structures from imaging artifacts. Within the ultrasound context, an artifact can be defined as an error in the perception or visual representation of ultrasound images produced by the underlying imaging process formation. The generation of ultrasound images relies on physical assumptions (e.g. speed of sound in tissue is constant, acoustic energy is uniformly attenuated, etc.) to assign the location and the intensity of each received echo. In reality, these assumptions usually are not maintained, and when this occurs, the returning echoes can be displayed erroneously, leading to artifacts.

The characteristic speckle pattern presented in all B-mode images is probably the most important and well-known artifact. It arises from the constructive/destructive interference of ultrasound waves as they travel from the transducer into the body and back. The skilled sonographer can take advantage of this and other artifacts to obtain important information about the anatomy and the pathological condition under investigation. For example, a tumour can leave a shadow trace when interacting with the acoustic field, while a gas bubble does not. In that way, the artifact can be used to precisely identify the type of tissue under study and use this information to identify certain anatomical features. Because the physics of ultrasound waves are being modeled, some artifacts already naturally arise in the system; e.g., speckle, directional ambiguity, spectral broadening. However, other clinically relevant artifacts (e.g. shadowing, mirror images, speed propagation) do not.

The addition of these artifacts to the simulations performed by the system increase the realism and the variety of imaging conditions, as well as the number of pathological cases available to the sonographer.

Ray-tracing is a technique widely use in computer graphics for generating an image by tracing the path of light through pixels in an image plane and simulating the effects of its encounters with virtual objects. Prior approaches to applying ray-tracing suffer of the same limitations as physical phantoms (e.g., limited to predefined cases, inflexible because they cannot modify simulation parameters, etc.) owing to the assumption of a fixed point spread function (PSF), in contrast with the method used by the system that generates the ultrasound RF-signals directly.

The system 100 can combine the real-time ultrasound simulation method with a sound-ray tracing approach to account for shadowing effects, object refraction, and speed propagation artifacts. The sound-ray-tracing algorithm is used to follow the path from the transducer surface towards the axial direction of every ultrasound line along the ultrasound field of view and their intersection(s) with the 3D organ(s) under study, as shown in FIG. 11C. In this manner, the method used by the system 100 is inherently crossing boundaries within the 3D models as the ray is traveling from the transducer towards the organs under study. In addition, a specific speed propagation value can be assigned to each individual scatterer according to the characteristics of the type of tissue. This information can be combined and used to alter the phases and amplitudes of the simulated RF signal generated by the system, further refining the appearance of the ultrasound images to be more like that shown in FIG. 11D. A key advantage of using the sound-ray-tracing algorithm is that GPUs accelerate ray-tracing algorithms in computer graphics complex illumination environments, so gains in realism can be achieved with no significant impact on performance.

CFD is employed by the system 100 to solve the flow equations for a given set of boundary conditions, producing a velocity field at all discrete spatial locations within the mesh representation of the vessel for a discrete set of time instances. The computation of particle trajectories by the system 100 is a post-processing step of the resulting velocity field data, and is used to extract a smaller set of data representing flow in the vessel. Using particle trajectories to describe the flow in a complex arterial geometry is a computation simplification in contrast with using traditional CFD methods, and is thus more suitable for use in a real-time system.

Particle trajectories have encoded information of the flow field in space and time, so it is possible to compute a set of scatter positions that pass through the sample volume location. To do so, it is necessary to identify which particle trajectories are passing through this location. This can be done by using a spatial division algorithm, such as octree. Once the target trajectories are identified, corresponding point scatters have to be computed.

Because the trajectories are represented as discrete point-segments with time and flow velocity information encoded, it could happen that, for a given spatial position within the SV, there is no matching time information for that given trajectory and given sample time. In this case, any interpolation method can be used to compute the missing scatter locations.

Although the foregoing has been described with reference to certain specific embodiments, various modifications thereto will be apparent to those skilled in the art without departing from the spirit and scope of the invention as outlined in the appended claims. The entire disclosures of all references recited above are incorporated herein by reference.

The invention claimed is:

1. A method for simulating ultrasound imaging, the method comprising:
   storing a model of a sham ultrasound transducer held by an operator during a simulated ultrasound procedure as a plurality of point sources for emitting a simulated acoustic wave during the simulated ultrasound procedure;
   storing an ultrasound target model;
   calculating a plurality of radio-frequency signals by repeatedly:
      calculating the emission of a simulated acoustic wave signal from each point source to a subset of the ultrasound target model;

calculating a transmitted impulse response for the subset of the ultrasound target model;
calculating an overall transmitted impulse by aggregating the transmitted impulse responses;
calculating an overall transmit-receive impulse response from the overall transmitted impulse response; and
calculating a radio frequency signal from the overall transmit-receive impulse response; and
generating an ultrasound image for output to a display from the plurality of radio frequency signals.

2. The method of claim 1, wherein the ultrasound target model comprises a plurality of point scatterers, wherein the emission of the simulated acoustic wave is calculated from each point source to each point scatterer in the subset of the ultrasound target model, and wherein the transmitted impulse response is calculated for each point scatterer in the subset of the ultrasound target model.

3. The method of claim 2, wherein calculating the transmitted impulse response comprises using a phase of each acoustic wave signal between each point source and each point scatterer in the subset to compute a plurality of impulses, the phase being proportional to a distance between each point source in the subset and each point reflector.

4. The method of claim 2, further comprising receiving pre-computed computational fluid dynamics flow information for the ultrasound target, associating the pre-computed computational fluid dynamics information with each point scatterer of the subset, and outputting a Doppler ultrasound image by post processing the plurality of radiofrequency signals and the computational fluid dynamics information.

5. The method of claim 2, wherein the ultrasound target comprises a three-dimensional model of an organ and the plurality of point scatterers are randomly distributed within the three-dimensional model of the organ.

6. The method of claim 2, further comprising:
segmenting the ultrasound target model into a plurality of regions;
associating each point scatterer with one of the plurality of regions;
defining a sample volume as a volume where simulated acoustic energy from the simulated acoustic wave is concentrated during a simulated ultrasound procedure;
determining a subset of the plurality of regions that fully encompass the sample volume; and
determining the subset of the point scatterers associated with the subset of the plurality of regions during a simulated ultrasound procedure.

7. The method of claim 2, further comprising:
defining a sample volume as a volume where simulated acoustic energy from the simulated acoustic wave exceeds a predetermined threshold criterion, the threshold criterion being proportional to the power of the simulated acoustic energy; and
determining the subset of the point scatterers that fall within the sample volume.

8. The method of claim 1, wherein the ultrasound target model comprises a three-dimensional ("3D") triangulated surface mesh, wherein the emission of the simulated acoustic wave is calculated via ray-tracing from each point source to the 3D triangulated surface mesh, and wherein the transmitted impulse response is calculated for each ray from the 3D triangulated surface mesh.

9. The method of claim 1, wherein calculating a plurality of radio-frequency signals comprises:
determining the position and orientation of the sham transducer relative to the simulated location of an ultrasound target via a 3D position sensor and a 3D positioning reference module.

10. A system for simulating ultrasound imaging, the system comprising:
at least one processor;
storage storing a model of a sham ultrasound transducer held by an operator during a simulated ultrasound procedure as a plurality of point sources for emitting a simulated acoustic wave during the simulated ultrasound procedure, and an ultrasound target model, and computer-readable instructions that, when executed by the at least one processor, cause the processor to:
calculate a plurality of radio-frequency signals by repeatedly:
calculate the emission of a simulated acoustic wave signal from each point source to a subset of the ultrasound target model;
calculate a transmitted impulse response for the subset of the ultrasound target model;
calculate an overall transmitted impulse by aggregating the transmitted impulse responses;
calculate an overall transmit-receive impulse response from the overall transmitted impulse response; and
calculate a radio frequency signal from the overall transmit-receive impulse response; and
generate an ultrasound image for output to a display from the plurality of radio frequency signals.

11. The system of claim 10, wherein the ultrasound target model comprises a plurality of point scatterers, wherein the emission of the simulated acoustic is calculated from each point source to each point scatterer in the subset of the ultrasound target model, and wherein the transmitted impulse response is calculated for each point scatterer in the subset of the ultrasound target model.

12. The system of claim 11, wherein the computer-readable instructions, when executed, cause the at least one processor to use a phase of each acoustic wave signal between each point source and each point scatterer in the subset to compute a plurality of impulses, the phase being proportional to a distance between each point source in the subset and each point reflector.

13. The system of claim 11, wherein the computer-readable instructions, when executed, cause the at least one processor to receive pre-computed computational fluid dynamics flow information for the ultrasound target, associate the pre-computed computational fluid dynamics information with each point scatterer of the subset, and output a Doppler ultrasound image by post processing the plurality of radiofrequency signals and the computational fluid dynamics information.

14. The system of claim 11, wherein the ultrasound target comprises a 3D model of an organ and the plurality of point scatterers are randomly distributed within the 3D model of the organ.

15. The system of claim 11, wherein the computer-readable instructions, when executed, cause the at least one processor to:
segment the ultrasound target model into a plurality of regions;
associate each point scatterer with one of the plurality of regions;
define a sample volume as a volume where simulated acoustic energy from the simulated acoustic wave is concentrated during a simulated ultrasound procedure;
determine a subset of the plurality of regions that fully encompass the sample volume; and determine the subset of the point scatterers associated with the subset of the plurality of regions during a simulated ultrasound procedure.

16. The system of claim 11, wherein the computer-readable instructions, when executed, cause the at least one processor to:
define a sample volume as a volume where simulated acoustic energy from the simulated acoustic wave exceeds a predetermined threshold criterion, the threshold criterion being proportional to the power of the simulated acoustic energy; and
determine the subset of the point scatterers that fall within the sample volume.

17. The system of claim 10, wherein the ultrasound target model comprises a three-dimensional ("3D") triangulated surface mesh, and wherein the computer-readable instructions, when executed, cause the at least one processor to calculate the emission of the simulated acoustic via ray-tracing from each point source to the 3D triangulated surface mesh, and calculate the transmitted impulse response for each ray from the 3D triangulated surface mesh.

18. The system of claim 10, wherein the computer-readable instructions, when executed, cause the at least one processor to determine the position and orientation of the sham transducer relative to the simulated location of an ultrasound target via a 3D position sensor and a 3D positioning reference module.

19. The system of claim 10, wherein the computer-readable instructions, when executed, cause the at least one processor to calculate the overall transmit-receive impulse response by self-convoluting the overall transmitted impulse response.

20. A method for simulating ultrasound imaging, the method comprising:
storing a model of a sham ultrasound transducer held by an operator during a simulated ultrasound procedure as a plurality of point sources for emitting a simulated acoustic wave and as a fixed volume of transducer scatterers, the transducer scatterers being in a fixed spatial relationship from the plurality of point sources;
storing a model of an ultrasound target as a plurality of model scatterers, wherein each model scatterer has an associated reflection coefficient;
pre-computing impulse responses for each transducer scatterer in the fixed volume of transducer scatterers to a simulated acoustic wave emitted from the plurality of point sources; and
upon the fixed volume of transducer scatterers at least partly intersecting the plurality of model scatterers during the simulated ultrasound procedure:
determining, for each transducer scatterer, a nearest neighbor model scatterer;
assuming, for each transducer scatterer, the associated reflection coefficient of its nearest neighbor scatterer; and
scaling the pre-computed impulse responses with the associated reflection coefficients.

* * * * *